(12) United States Patent
De Ridder

(10) Patent No.: US 10,668,288 B2
(45) Date of Patent: *Jun. 2, 2020

(54) SYSTEM AND METHOD FOR NESTED NEUROSTIMULATION

(71) Applicant: Dirk De Ridder, Dunedin (NZ)

(72) Inventor: Dirk De Ridder, Dunedin (NZ)

(*) Notice: Subject to any disclaimer, the term of this patent is extended or adjusted under 35 U.S.C. 154(b) by 0 days.

This patent is subject to a terminal disclaimer.

(21) Appl. No.: 16/133,521

(22) Filed: Sep. 17, 2018

(65) Prior Publication Data

US 2019/0015666 A1 Jan. 17, 2019

Related U.S. Application Data

(63) Continuation of application No. 14/851,540, filed on Sep. 11, 2015, now Pat. No. 10,076,668.

(60) Provisional application No. 62/049,086, filed on Sep. 11, 2014.

(51) Int. Cl.
*A61N 1/00* (2006.01)
*A61N 1/36* (2006.01)
*A61N 1/05* (2006.01)

(52) U.S. Cl.
CPC ..... *A61N 1/36171* (2013.01); *A61N 1/36139* (2013.01); *A61N 1/36192* (2013.01); *A61N 1/36196* (2013.01); *A61N 1/0529* (2013.01); *A61N 1/0551* (2013.01); *A61N 1/36067* (2013.01); *A61N 1/36082* (2013.01); *A61N 1/36178* (2013.01)

(58) Field of Classification Search
CPC .. A61N 1/0526; A61N 1/0529; A61N 1/0531; A61N 1/0534; A61N 1/0541; A61N 1/36171; A61N 1/36178; A61N 1/36164
See application file for complete search history.

(56) References Cited

U.S. PATENT DOCUMENTS

| | | | | |
|---|---|---|---|---|
| 5,983,141 A * | 11/1999 | Sluijter | ................. | A61N 1/403 607/100 |
| 2006/0095088 A1* | 5/2006 | De Ridder | ........... | A61N 1/0529 607/48 |
| 2009/0093858 A1* | 4/2009 | DiUbaldi | ............. | A61N 1/0514 607/17 |
| 2014/0081348 A1* | 3/2014 | Fischell | ............. | A61N 1/36067 607/45 |

\* cited by examiner

*Primary Examiner* — Mallika D Fairchild

(57) ABSTRACT

A method and system are provided to deliver nested stimulation to brain tissue of interest. The method and system set first parameters that define a carrier waveform. The method and system set second parameters that define a high frequency waveform, wherein at least one of the carrier waveform and high frequency waveform are defined to correspond to physiologic neural oscillations associated with the brain tissue of interest. The method and system operates a pulse generator to generate a nested stimulation waveform that combines the carrier waveform and high frequency waveform. The nested stimulation waveform has a plurality of pulse bursts. The method and system deliver the nested stimulation waveform through one or more electrodes to the brain tissue of interest.

9 Claims, 16 Drawing Sheets

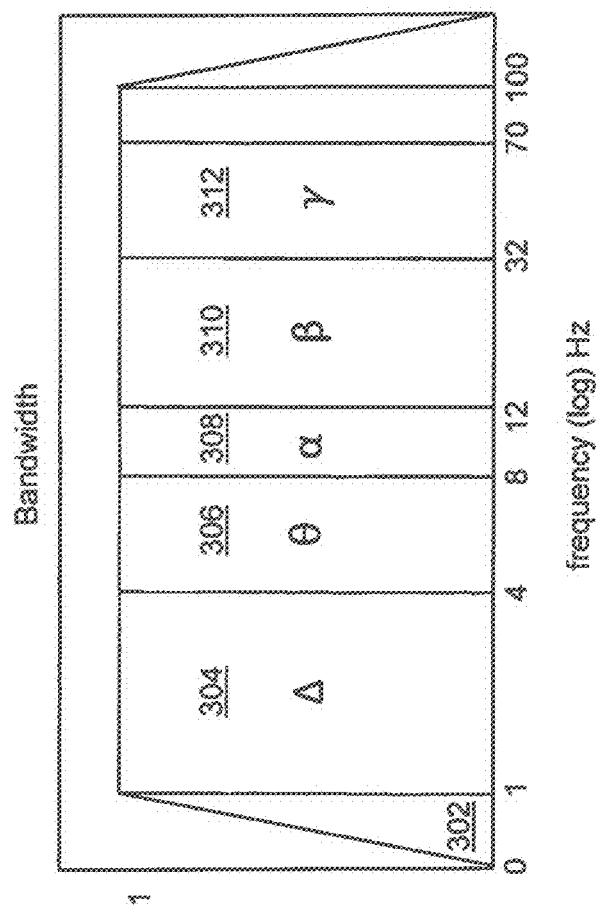

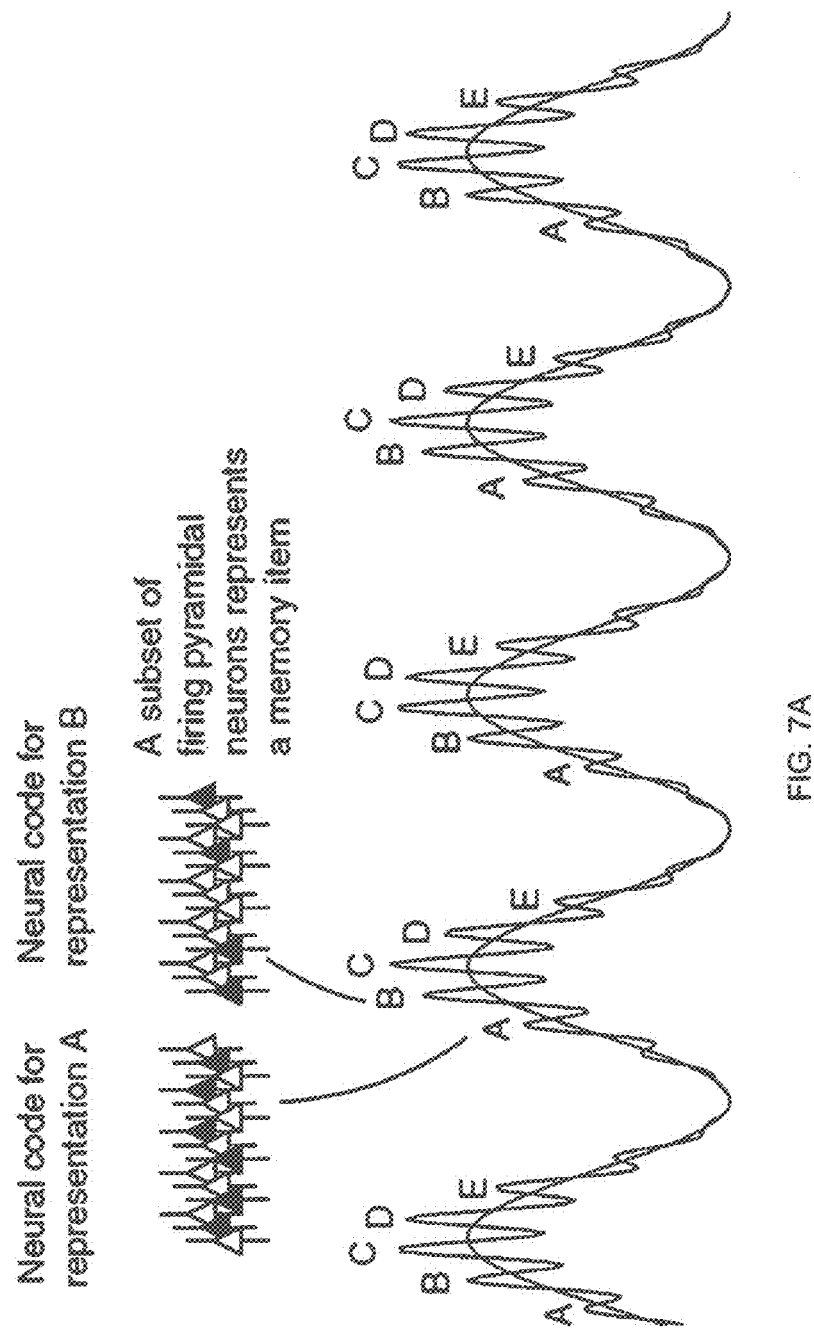

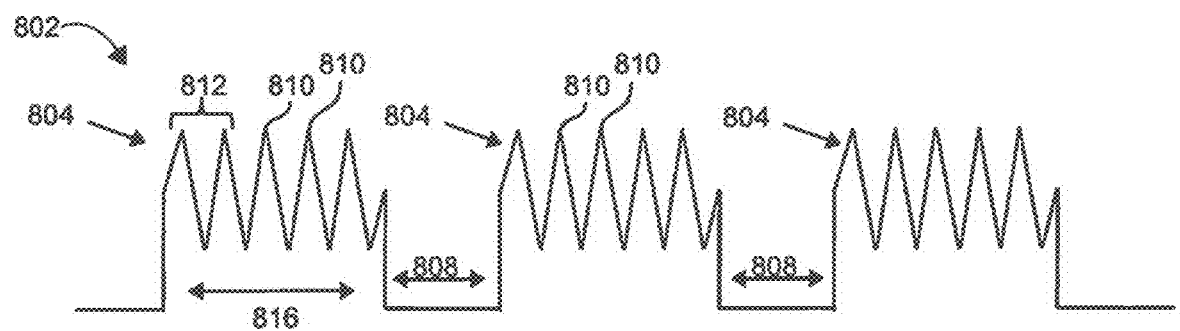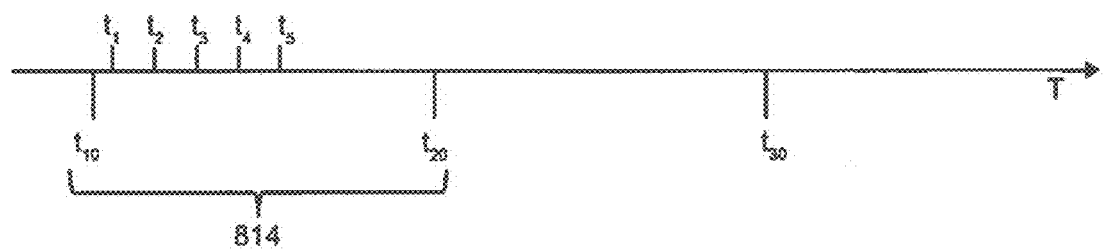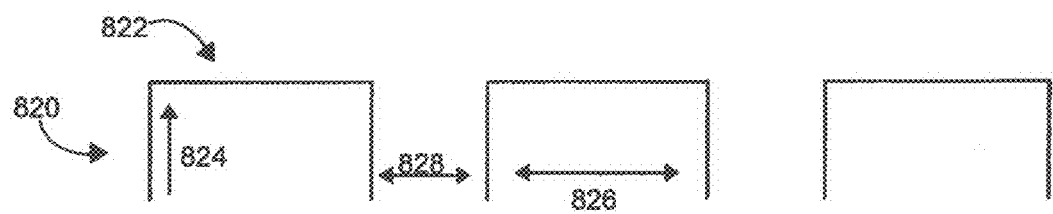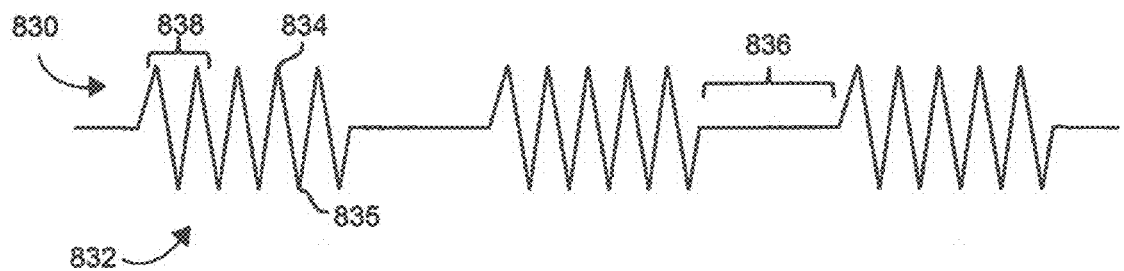
FIG. 8A

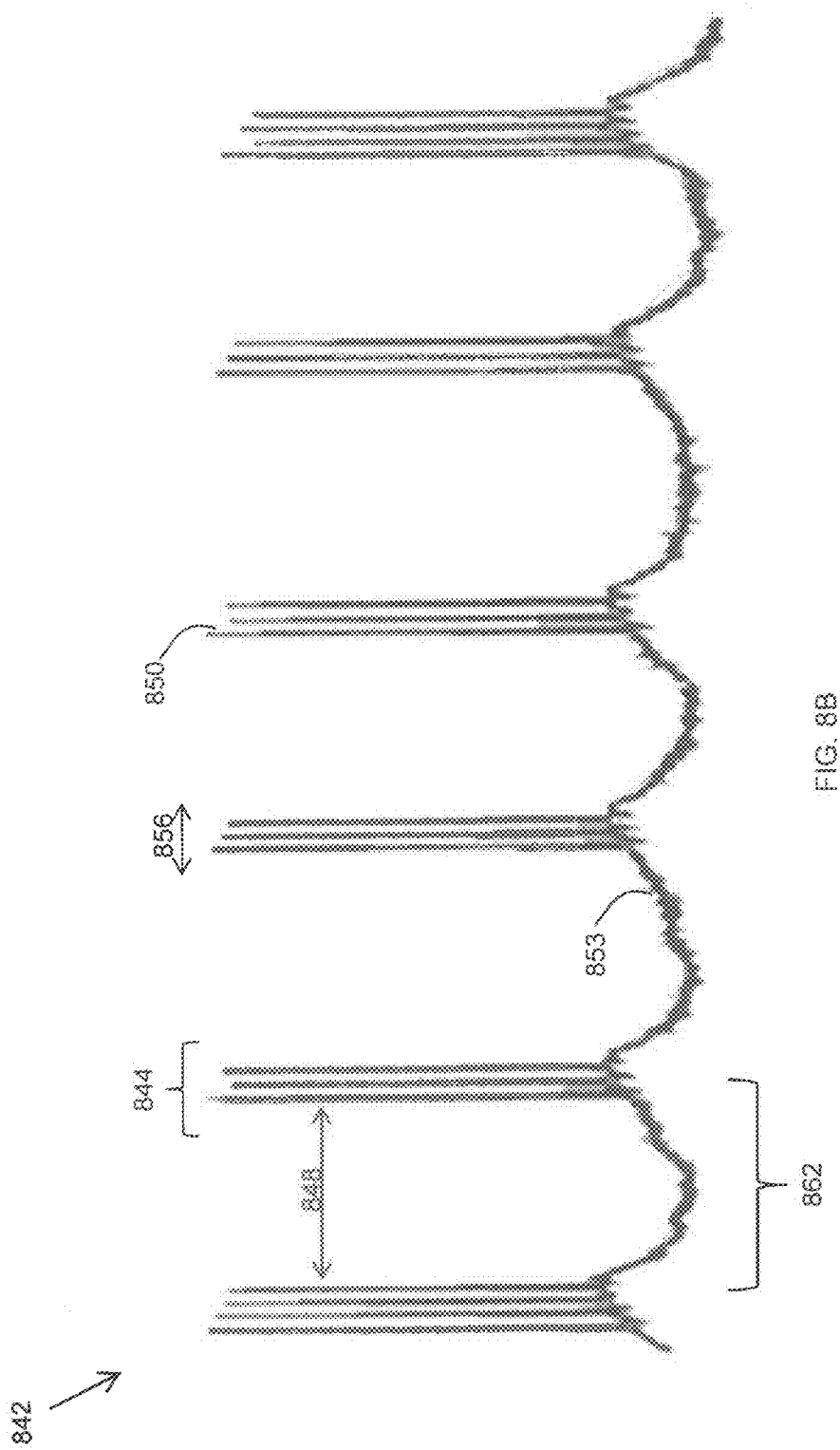

SYSTEM AND METHOD FOR NESTED NEUROSTIMULATION

The present application is a continuation of U.S. patent application Ser. No. 14/851,540 filed Sep. 11, 2015 and claims priority to U.S. Patent Application Ser. No. 62/049,086 filed Sep. 11, 2014, titled "NESTED NEUROSTIMULATION", the complete subject matter of which is incorporated herein by reference in its entirety.

BACKGROUND OF THE INVENTION

Embodiments of the present disclosure generally relate to neurostimulation (NS), and more particularly to delivering nested neurostimulation.

NS systems are devices that generate electrical pulses and deliver the pulses to nervous tissue to treat a variety of disorders. For example, spinal cord stimulation has been used to treat chronic and intractable pain. Another example is deep brain stimulation, which has been used to treat movement disorders such as Parkinson's disease and affective disorders such as depression. SCS therapy, delivered via epidurally implanted electrodes, is a widely used treatment for chronic intractable neuropathic pain of different origins. Traditional tonic therapy evokes paresthesia covering painful areas of a patient. During SCS therapy calibration, the paresthesia is identified and localized to the painful areas by the patient in connection with determining correct electrode placement.

Recently, new stimulation configurations such as burst stimulation and high frequency stimulation, have been developed, in which closely spaced high frequency pulses are delivered. In general, conventional neurostimulation systems seek to manage pain and other pathologic or physiologic disorders through stimulation of select nerve fibers that carry pain related signals. However, nerve fibers and brain tissue carry other types of signals, not simply pain related signals.

A need remains for methods and systems that deliver therapies that stimulate brain tissue, in order to override or alter pathological neural oscillations to treat a neurological condition.

SUMMARY

In accordance with embodiments herein a method is provided to deliver nested stimulation to nerve tissue of interest. The nerve tissue of interest may represent various types of nerve tissue, such as brain tissue, spinal cord tissue, dorsal root ganglion tissue and the like. The method comprises setting first parameters that define a carrier waveform. The method further provides setting second parameters that define a high frequency waveform, wherein at least one of the carrier waveform and high frequency waveform are defined to correspond to physiologic neural oscillations associated with the nerve tissue of interest. The method further operates a pulse generator to generate a nested stimulation waveform that combines the carrier waveform and high frequency waveform. The nested stimulation waveform has a plurality of pulse bursts. The method delivers the nested stimulation waveform through one or more electrodes to the nerve tissue of interest.

Optionally, the high frequency waveform corresponds to high-frequency physiologic neural oscillations associated with the nerve tissue of interest. The pulse bursts includes pulses may have a frequency corresponding to the high frequency neural oscillations. The carrier waveform may correspond to low-frequency physiologic neural oscillations associated with the nerve tissue of interest. The pulse bursts are separated from one another with a burst to burst period that corresponds to a frequency of the low-frequency neural oscillations. The first and second parameters define at least one of an amplitude, burst to burst frequency, pulse frequency, pulse width, burst length and burst period for the plurality of pulse bursts. The method further comprises combining the carrier and high-frequency waveforms utilizing one of the following types of cross frequency coupling: power to power; phase to power; phase to phase; phase to frequency; power to frequency and frequency to frequency.

Optionally, the carrier and high-frequency waveforms are combined through phase to power cross frequency coupling, in which the phase of the carrier waveform modulates the power of the high-frequency waveform. The first parameters may be set to define the carrier waveform to correspond to the theta wave frequency band, while the second parameters may be set to define the high-frequency waveform to correspond to the gamma wave frequency band. The method further comprises managing the nested stimulation waveform modulating the neural oscillations in the gamma wave frequency band in connection with at least one of sensory, motor, and cognitive events. The method manages the nested stimulation waveform in connection with an event of interest through cross frequency coupling between theta and gamma waves associated with the nerve tissue of interest.

The nerve tissue of interest may comprise distributed neural modules located in separate regions of the brain. Optionally, the method further comprises managing the nested stimulation waveform in connection with cross frequency coupling between neural oscillations associated with the distributed neural modules that exhibit long-distance communication over neural oscillations within at least one of delta, theta and alpha wave frequency bands. Optionally, the method measures intrinsic neural oscillations, determines whether the nested stimulation waveform is achieving entrainment of the intrinsic neural oscillations, and adjusts at least one of the first and second parameters to maintain entrainment of the intrinsic neural oscillations.

In accordance with embodiments herein a system is provided to deliver nested stimulation to nerve tissue of interest. The system comprises a lead having an array of stimulation electrodes. The lead is configured to be implanted at a target position proximate to nerve tissue of interest. An implantable medical device (IMD) is coupled to the lead. The IMD includes a processor and memory storing programmable instructions. The processor executes the programmable instructions to set first parameters that define a carrier waveform. Further the processor sets second parameters that define a high frequency waveform, wherein at least one of the carrier waveform and high frequency waveform are defined to correspond to physiologic neural oscillations associated with the nerve tissue of interest. The processor further operates a pulse generator to generate a nested stimulation waveform that combines the carrier waveform and high frequency waveform, the nested stimulation waveform having a plurality of pulse bursts; and delivers the nested stimulation waveform through one or more electrodes to the nerve tissue of interest.

Optionally, the high frequency waveform corresponds to high-frequency physiologic neural oscillations associated with the nerve tissue of interest, and the pulse bursts including pulses having a frequency corresponding to the high frequency physiologic neural oscillations. The carrier waveform corresponds to low-frequency physiologic neural oscillations associated with the nerve tissue of interest. The pulse bursts are separated from one another with a burst to burst period that corresponds to a frequency of the low-frequency neural oscillations. The first and second parameters define at least one of an amplitude, burst to burst frequency, pulse frequency, pulse width, burst length and burst period for the plurality of pulse bursts.

Optionally, the processor combines the carrier and high-frequency waveforms utilizing one of the following types of cross frequency coupling: power to power; phase to power; phase to phase; phase to frequency; power to frequency and frequency to frequency. The processor may combine the carrier and high-frequency waveforms through phase to power cross frequency coupling, in which the phase of the carrier waveform modulates the power of the high-frequency waveform.

The brain tissue of interest may comprise distributed neural modules located in separate regions of the brain. The processor manages the nested stimulation waveform in connection with cross frequency coupled between neural oscillations associated with the distributed neural modules that exhibit long-distance communication over neural oscillations within at least one of delta, theta and alpha wave frequency bands. Optionally, the lead includes sensing electrodes. The processor measures intrinsic neural oscillations through the sensing electrodes, determines whether the nested stimulation waveform is achieving entrainment of the intrinsic neural oscillations, and adjusts at least one of the first and second parameters to maintain entrainment of the intrinsic neural oscillations.

BRIEF DESCRIPTION OF THE DRAWINGS

FIG. 3 illustrates an example of the various brainwave frequency bands in accordance with embodiments herein.

FIG. 7A illustrates models proposed, in the 2007 Jensen paper, regarding computational roles for cross-frequency interactions between theta and gamma oscillations by means of phase coding in accordance with embodiments herein.

FIG. 8A illustrates an example of a nested stimulation waveform that may be delivered in connection with nested therapies to brain tissue (or brain tissue) of interest in accordance with embodiments herein.

FIG. 8B illustrates an example of a nested stimulation waveform that may be delivered in connection with nested therapies to brain tissue (or brain tissue) of interest in accordance with embodiments herein.

DETAILED DESCRIPTION

Figure 1A:
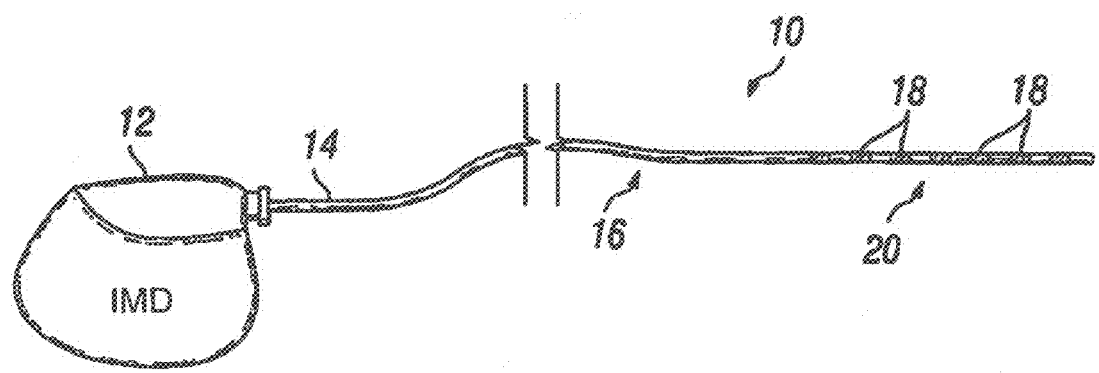
FIG. 1A illustrates an example neurological stimulation (NS) system for electrically stimulating a predetermined site area to treat one or more neurological disorders or conditions in accordance with embodiments herein.

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

I. Definitions

Unless defined otherwise, technical and scientific terms used herein have the same meaning as commonly understood by one of ordinary skill in the art to which this invention belongs. For purposes of the description, the following terms are defined below. Further, additional terms are used herein that shall have definitions consistent with the definitions set forth in U.S. Pat. No. 8,401,655, which is expressly incorporated herein by reference in its entirety.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having", "including", "containing" and "comprising" are interchangeable and one of skill in the art is cognizant that these terms are open ended terms.

As used herein, the term "burst firing" or "burst mode" refers to an action potential that is a burst of high frequency spikes/pulses (e.g. 400-1000 Hz) (Beurrier et al., 1999). Burst firing acts in a non-linear fashion with a summation effect of each spike/pulse. One skilled in the art is also aware that burst firing can also be referred to as phasic firing, rhythmic firing (Lee 2001), pulse train firing, oscillatory firing and spike train firing, all of these terms used herein are interchangeable.

As used herein, the term "tonic firing" or "tonic mode" refers to an action potential that occurs in a linear fashion.

As used herein, the term "burst" refers to a period in a spike train that has a much higher discharge rate than surrounding periods in the spike train (N. Urbain et al., 2002). Thus, burst can refer to a plurality of groups of spike pulses. A burst is a train of action potentials that, possibly, occurs during a 'plateau' or 'active phase', followed by a period of relative quiescence called the 'silent phase' (Nunemaker, Cellscience Reviews Vol 2 No. 1, 2005.) Thus, a burst comprises spikes having an inter-spike interval in which the spikes are separated by 0.5 milliseconds to about 100 milliseconds. Those of skill in the art realize that the inter-spike interval can be longer or shorter. Yet further, those of skill in the art also realize that the spike rate within the burst does not necessarily occur at a fixed rate; this rate can be variable.

The terms "pulse" and "spike" are used interchangeably to refer to an action potential. Yet further, a "burst spike" refers to a spike that is preceded or followed by another spike within a short time interval (Matveev, 2000), in other words, there is an inter-spike interval, in which this interval is generally about 100 ms but can be shorter or longer, for example 0.5 milliseconds.

Embodiments herein are described for methods and systems that seek to modify brain wave activity in connection with treating various pathologic disorders.

Different firing modes or frequencies of neural oscillations occur in the brain and/or other neuronal tissue, for example tonic firing and burst firing (irregular or regular burst firing). The thalamus utilizes both types of firing modes. The two thalami (bilateral paired structures) are the gateways to the cerebral cortex and, thus, to consciousness. The thalamic nuclei specialize in several different signaling functions: transmitting signals from sensory input to the cortex; transmitting signals from cortical motor centers to effectors; transmitting control signals that select which input and output will be permitted to pass to and from the cortex and how the signals will be sequenced (thalamic reticular nuclei (TRN)); and modulating (controlling intensity) and synchronizing (grouping) the signals (Intralaminar Nuclei (ILN)).

All thalamic relay neurons pass through the TRN, which opens and closes their "gates" going to the cortex, (McAlonan and Brown, 2002). One mode that TRN neurons use to transmit these relays is burst firing mode. This mode is useful for activating a small population of neurons in the cortex for a short period. In contrast, the continuous (tonic) firing mode permits a thalamic neuron to transmit a steady stream of signals to the cortex. The tonic firing pattern triggers looping activation in the cortical circuits that receive the signals. Evoking looping, or "recurrent" activation in the cortex requires a steady neural input.

In general, humans display different types of neural oscillations or "brain waves" across the cortex. The different types of neural oscillation or brain wave activity can be decomposed into distinct frequency bands that are associated with particular physiologic and pathologic characteristics. FIG. 3 illustrates an example of the various brainwave frequency bands which include infraslow waves 302 (less than 1 Hz); delta waves 304 (1-4 Hz); theta waves 306 (4-8 Hz); alpha waves 308 (8-12 Hz), beta waves 310 (12-30 Hz), gamma waves 312 (greater than 30 Hz), and sigma waves (not shown) (greater than 500 Hz). Individual brainwave frequency bands and combinations of brainwave frequency bands are associated with various mental, physical and emotional characteristics. It should be recognized that the cutoff frequencies for the frequency bands for the various types of brain waves are approximations. Instead, the cutoff frequencies for each frequency band may be slightly higher or lower than the examples provided herein.

Neural oscillations from various combinations of the brainwave frequency bands have been shown to exhibit coupling with one another, wherein one or more characteristics of one type of brainwave effect (or are affected by) one or more characteristics of another type of brainwave. In general, the coupling phenomenon is referred to as cross frequency coupling, various aspects of which are described in the papers referenced herein. Combinations of frequency bands couple with one another to different degrees, while the coupling of various types of brainwaves may occur in connection with physiologic behavior or pathologic behavior. For example, theta and gamma frequency coupling has been identified at the hippocampalcortical in connection with physiologic behavior. delta-gamma and delta-beta frequency coupling have been identified in connection with pathologic limbic dysrhythmia. As another example, alpha-gamma frequency coupling has been identified at the pulvinar region in connection with pathologic thalamocortical dysrhythmia.

In general, higher frequency brainwave neural oscillations are at least loosely coupled to one or more lower frequency brainwave neural oscillations. For example, the phase of delta waves has been found to modulate the amplitude of theta waves. Further, theta waves have been found to modulate the amplitude of gamma waves.

Optionally, more than one level of coupling or nesting may be achieved such as through a nesting hierarchy in which one or more high frequency ranges nest with one or more low frequency ranges. For example, combinations of the following frequency ranges may couple/nest with one another: infraslow (0.01-1 Hz), delta (1-3 Hz), theta (4-7 Hz), alpha (8-12 Hz), beta (13-30 Hz), gamma (31-100 Hz) to ultrafast waves (>100 Hz-1200 Hz). When a nesting hierarchy occurs, an intermediate or higher frequency range may itself become a carrier wave for an even higher frequency wave. For example, delta waves may represent a carrier for beta waves, while the beta waves represent a carrier for gamma or ultrafast waves.

Figure 4:
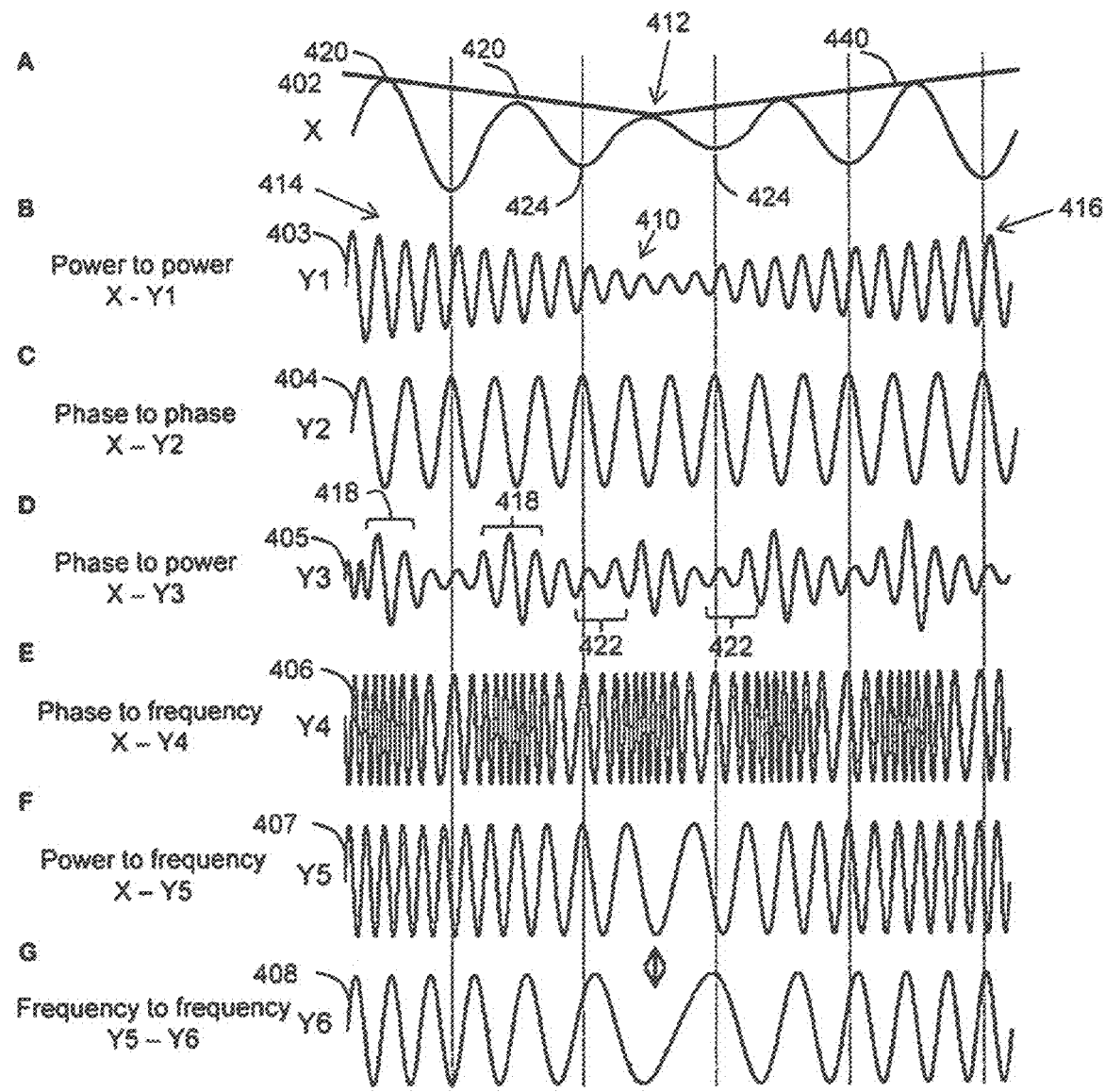
FIG. 4 illustrates examples of cross frequency coupling variations that may be used in accordance with embodiments herein.

FIG. 4 illustrates examples of cross frequency coupling variations that may be used in accordance with embodiments herein. There are different principles of cross-frequency interactions. FIG. 4 illustrates various example brain waves 402-408. As one example, a carrier wave 402 may correspond to a slow oscillatory signal in the theta band (e.g. 8 Hz). Although the frequency remains fairly constant, the power (as denoted by line 440) of the signal fluctuates over time. The gamma oscillations can interact in different ways with other signal oscillations.

The brain waves 403-408 illustrate examples of how the carrier and secondary waves 402 and 403 may be combined. For example, the wave 403 as illustrated has been frequency coupled to the carrier wave 402 in a power to power matter such that the amplitude of the secondary wave 402 reduces (as denoted at intermediate region 410) as the amplitude of the carrier wave 402 reduces (as denoted in region 412). The amplitude of the secondary wave 403 is at a maximum in the regions 414 and 416 corresponding to the maximum amplitudes of the carrier wave 402. The fluctuations in power of the faster gamma oscillations are correlated with power changes in the lower frequency band. This interaction is independent of the phases of the signals.

The brainwave 404 represents the carrier and secondary waves 402 and 403, as frequency coupled in a phase to phase manner. Given that the carrier and secondary waves 402 and 403 are aligned in phase with one another, the brainwave 404 exhibits a relatively even signal with little notable phase shift. Phase-locking occurs between oscillations at different frequencies. In each slow cycle, there are four faster cycles and their phase relationship remains fixed.

The brainwave 405 represents the carrier and secondary waves 402 and 403, as frequency coupled in a phase to power manner. For example, the amplitude of the resulting brainwave 405 is modulated based on the phase of the carrier wave 402. Accordingly, the brainwave 405 exhibits a maximum in amplitude in regions 418 which correspond to the positive 90° phase shift point (at reference numerals 420) in the carrier wave 402. The brainwave 405 exhibits a minimum amplitude in regions 422 which correspond to the negative 90° phase shift point (at reference numerals 424) in the carrier wave 402. Hence, in the example of brainwave 405, the amplitude of the higher frequency brainwave is modulated/determined by the phase of the lower frequency carrier wave.

The brain waves 406-408 reflect the carrier and secondary waves 402 and 403 when coupled in different manners, namely phase to frequency (brainwave 406), power to frequency (brainwave 407) and frequency to frequency (brainwave 408). It is recognized that the brain waves illustrated in FIG. 4 represent non-limiting examples and may be shaped in the numerous other manners. The different types of cross-frequency interaction are not mutually exclusive. For instance, the phase of theta oscillations might modulate both frequency and power of the gamma oscillations.

As explained herein, nested stimulation may be applied such that two, three or more frequency bands are coupled to one another to achieve various results. As noted above, the lower band represents a carrier wave with higher frequency bands nested on the lower carrier wave. The higher frequency bands carry content to be utilized by the targeted neural modules. For example, the high-frequency content may be superimposed into the phase of the lower carrier wave, such as in connection with external information transmission. Alternatively, the high-frequency content may be added while maintaining phase synchronization. Optionally, the high-frequency content may be added through amplitude or frequency modulation to the lower carrier wave. It is recognized that the high-frequency content may be added in other manners as well, based on the particular neural region of interest and desired effect that is being sought.

The brain organization is shaped by an economic trade-off between minimizing costs and allowing efficiency in connection with adaptive structural and functional topological connectivity patterns. For example, a low-cost, but low efficiency, organization would represent a regular lattice type topology. At an opposite end of the spectrum, a random topology would be highly efficient, but be more economically costly.

In general, the brain represents a modular scale free hierarchical network. The network comprises various regions or modules that are associated with different characteristics and activities. In accordance with embodiments herein, electrodes may be positioned proximate to various brain tissue of interest and generate nested stimulation waveforms. For example, the auditory cortex is the part of the temporal lobe that processes auditory information. The somatosensory cortex represents the main sensory receptive area for the sense of touch. The thalamus is a structure in the middle of the brain located between the cerebral cortex and the midbrain that correlates various processes such as consciousness, sleep and sensory interpretation. The cerebellum plays an important role in balance, motor control, but is also involved in some cognitive functions such as attention, language, emotional functions (such as regulating fear and pleasure responses) and in the processing of procedural memories. The cerebrum (or forebrain) is divided by a large groove, known as the longitudinal fissure, into two distinct hemispheres. The left and right hemispheres are linked by a large bundle of nerve fibers called the corpus callosum, and also by other smaller connections called commissures. Most of the elements of interest of the cerebrum, are split into symmetrical pairs in the left and right hemispheres. The right hemisphere generally controls the left side of the body, and vice versa, although popular notions that logic, creativity, etc., are restricted to the left or right hemispheres are largely simplistic and unfounded. The cerebrum is covered by a sheet of neural tissue known as the cerebral cortex (or neocortex), which envelops other brain organs such as the thalamus (which evolved to help relay information from the brain stem and spinal cord to the cerebral cortex) and the hypothalamus and pituitary gland (which control visceral functions, body temperature and behavioral responses such as feeding, drinking, sexual response, aggression and pleasure).

A large portion of the brain's neurons are located in the cerebral cortex, mainly in the "grey matter", which makes up the surface regions of the cerebral cortex, while the inner "white matter" consists mainly of myelinated axons. The cerebral cortex plays a role in memory, attention, perceptual awareness, thought, language and consciousness. It is divided into four main regions or lobes, which cover both hemispheres: the frontal lobe (involved in conscious thought and higher mental functions such as decision-making, particularly in that part of the frontal lobe known as the prefrontal cortex, and plays an important part in processing short-term memories and retaining longer term memories which are not task-based); the parietal lobe (involved in integrating sensory information from the various senses, and in the manipulation of objects in determining spatial sense and navigation); the temporal lobe (involved with the senses of smell and sound, the processing of semantics in both speech and vision, including the processing of complex stimuli like faces and scenes, and plays a key role in the formation of long-term memory); and the occipital lobe (mainly involved with the sense of sight).

The medial temporal lobe (the inner part of the temporal lobe, near the divide between the left and right hemispheres) in particular is thought to be involved in declarative and episodic memory. Deep inside the medial temporal lobe is the region of the brain known as the limbic system, which includes the hippocampus, the amygdala, the cingulate gyrus, the thalamus, the hypothalamus, the epithalamus, the mammillary body and other organs, many of which are of particular relevance to the processing of memory. The hippocampus, for example, is essential for memory function, particularly the transference from short- to long-term memory and control of spatial memory and behavior. The hippocampus is one of the few areas of the brain capable actually growing new neurons, although this ability is impaired by stress-related glucocorticoids. The amygdala also performs a primary role in the processing and memory of emotional reactions and social and sexual behavior, as well as regulating the sense of smell. Nested therapy may be delivered to the brain tissue regions to treat various pathologies.

It has been proposed that the number of gamma cycles per theta cycle determines the span of the working memory. It has been further proposed that the rate of item retrieval is consistent with the period of the gamma cycle (as measured in the Sternberg paradigm (Jensen 2007). It has been proposed the cross frequency interaction between gamma and theta oscillations are consistent with, and predictive of, expected working memory operations. Nested therapy may be utilized to treat disorders in the working memory.

Figure 5:
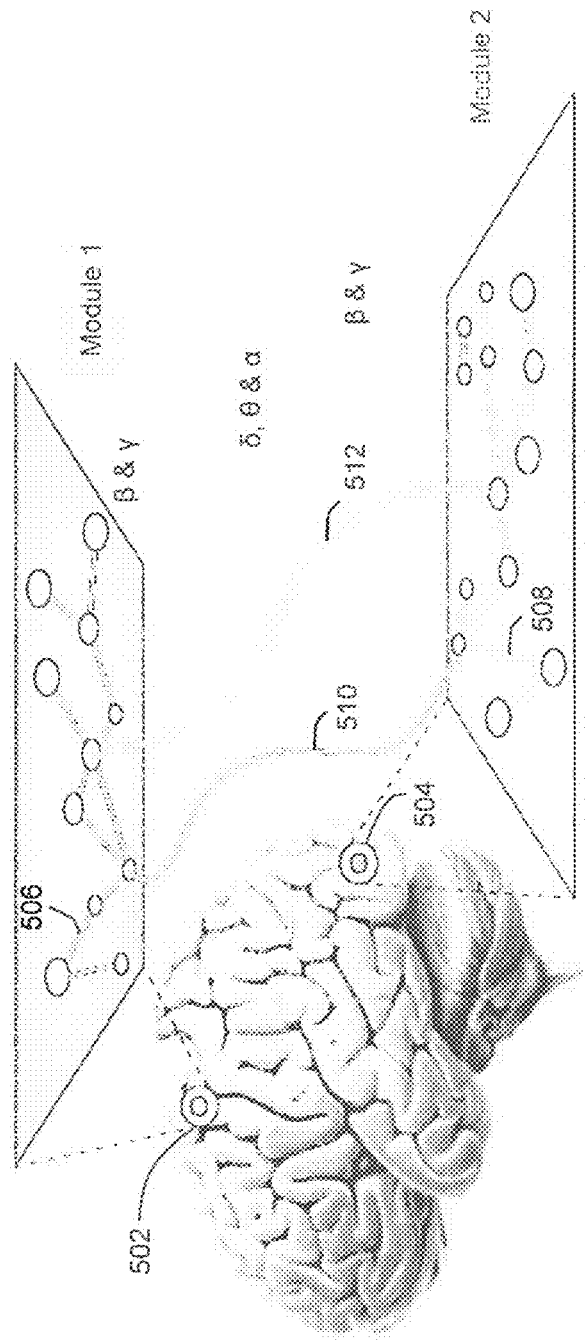
FIG. 5 illustrates a model of a portion of the brain with interest directed to neural modules in accordance with embodiments herein.

FIG. 5 illustrates a model of a portion of the brain with interest directed to neural modules 502 and 504. Local activity within modules 502 and 504 generally exhibits high frequency brain waves/oscillations (as generally denoted by the links 506 and 508). For example, the high-frequency brain waves/oscillations may represent beta and gamma waves. The neural modules 502 and 504 communicate with one another over long-distance communications links (as denoted at 510 and 512). The communications links 510, 512 between distributed neural modules 502, 504 occur through the use of low frequency brain waves (e.g. delta, Theta and Alpha waves). The communication between modules 502, 504 utilizes nesting or cross frequency coupling between the low frequency brain waves (traveling between distributed neural modules) and the high frequency brain waves (within corresponding neural modules). In this manner, transient coherence or phase synchronization binds distributed neural assemblies/modules within the brain through dynamic (and potentially long-range) connections. Nested therapy may be utilized to facilitate long-distance communication links. In accordance with embodiments herein, nested stimulation waveforms may be delivered directly or indirectly to one or more distributed neural modules 502, 504.

Figure 6:
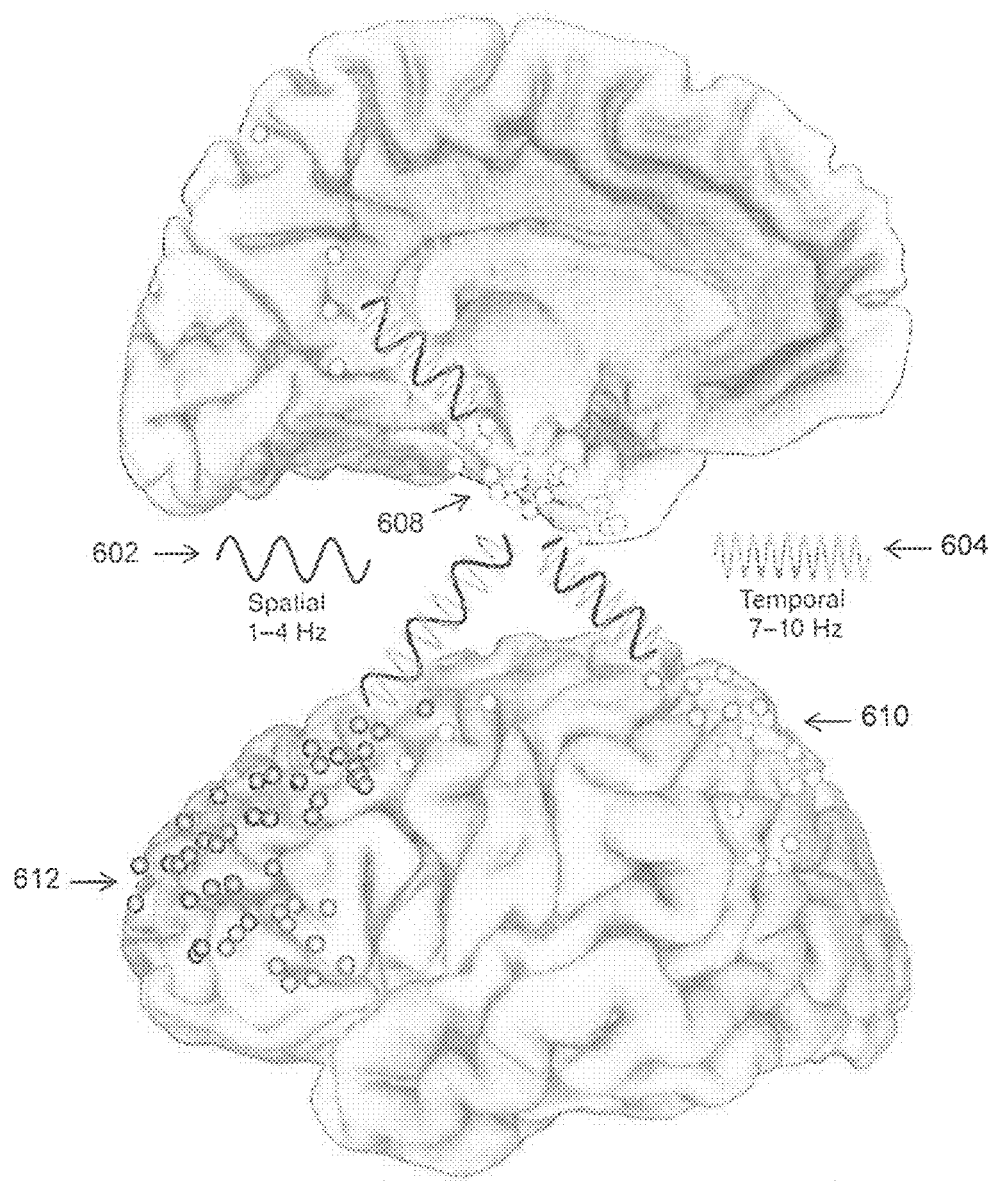
FIG. 6 illustrates a model reflecting the memory functionality of a brain in accordance with embodiments herein.

FIG. 6 illustrates a model reflecting the memory functionality of a brain. Memory has spatial and temporal characteristics 602 and 604. Memories are encoded through low frequency coupling between parahippocampal area 612, frontal area 608 and parietal (PFC) area 610. The spatial and temporal characteristics 602, 604 of memory are multiplexed along common pathways through different frequencies. For example, the spatial characteristics 602 of memory are carried within the delta wave frequency band, while the temporal characteristics 604 of memory are carried within the Alpha wave frequency band. Nested therapy may be utilized to facilitate spatial and/or temporal characteristics for memories.

Figure 7B:
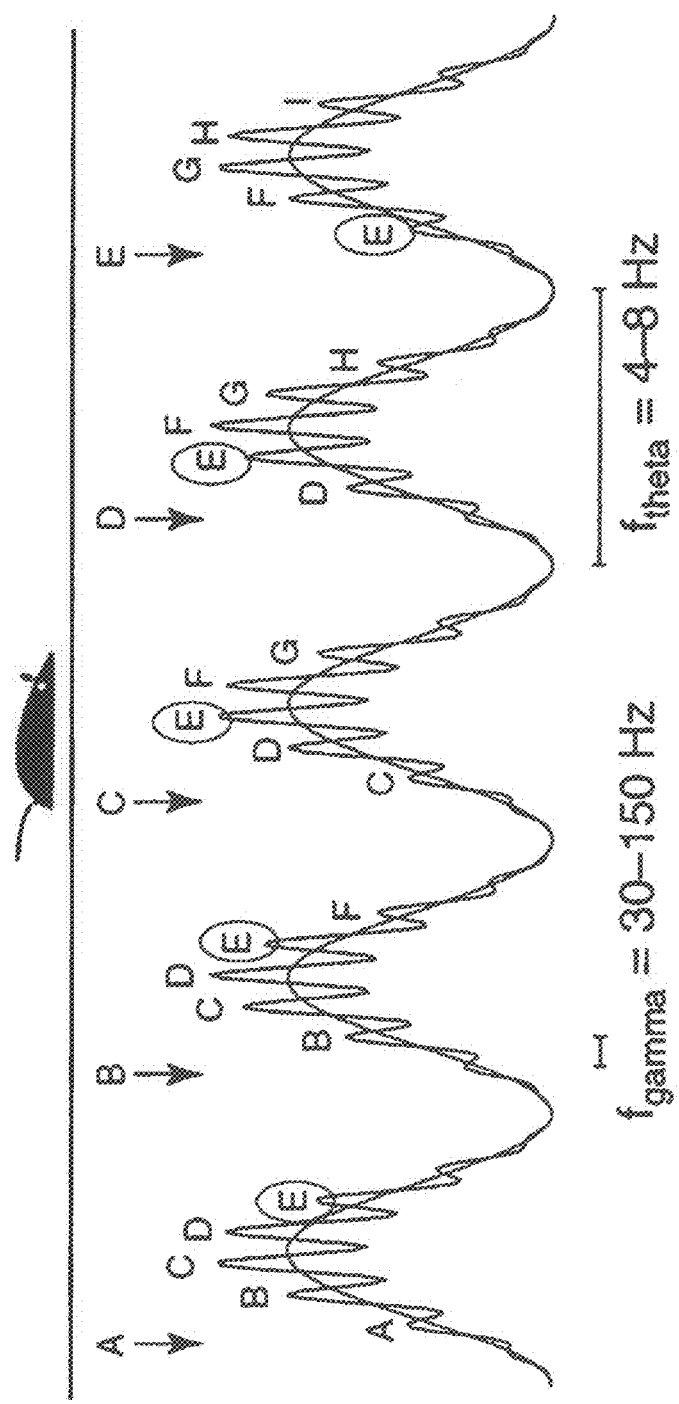
FIG. 7B illustrates models proposed, in the 2007 Jensen paper, regarding computational roles for cross-frequency interactions between theta and gamma oscillations by means of phase coding in accordance with embodiments herein.

FIGS. 7A and 7B illustrate models proposed, in the 2007 Jensen paper, regarding computational roles for cross-frequency interactions between theta and gamma oscillations by means of phase coding. FIG. 7A illustrates a model for working memory, in which individual memory representations are activated repeatedly in theta cycles. Each memory representation is represented by a subset of neurons in the network firing synchronously. Because different representations are activated in different gamma cycles, the gamma rhythm serves to keep the individual memories segmented in time. As reported by Jensen, the number of gamma cycles per theta cycle determines the span of the working memory. FIG. 7B illustrates a model accounting for theta phase precession in rats. Positional information is passed to the hippocampus, which activates the respective place cell representations and provokes the prospective recall of upcoming positions. In each theta cycle, time-compressed sequences are recalled at the rate of one representation per gamma cycle.

FIG. 8A illustrates an example of a nested stimulation waveform that may be delivered in connection with nested therapies to brain tissue (or brain tissue) of interest in accordance with embodiments herein. In FIG. 8A, the nested stimulation waveform 802 includes multiple pulse bursts 804 that are separated from one another by an inter-burst delay 808. Each of the pulse bursts 804 includes a series of individual pulses or spikes 810. The pulses 810 are delivered over a burst length 816 in connection with an individual pulse bursts 804. The rate at which the individual pulses 810 are delivered within a pulse bursts 804 is determined based on a pulse rate 812 (denoted as a bracket extending between successive positive peaks of adjacent successive pulses 810).

FIG. 8A also illustrates a timeline extending along a horizontal axis with various points in time noted along the nested stimulation waveform 802. Each of the successive pulse bursts 804 are initiated at start times T10, T20 and T30, respectively. The interval between successive start times (e.g. T10 and T20) represents the burst to burst period 814. The timeline also illustrates examples of the timing between pulses 810 within an individual pulse burst (e.g. 804). For example, pulse peak times T1-T5 are illustrated as aligned with the peak positive point of each pulse 810. The pulse rate 812 corresponds to the pulse to pulse period 814.

The nested stimulation waveform may be decomposed into at least two primary waveform components, generally denoted as a carrier waveform 820 and a high-frequency waveform 830. In accordance with embodiments herein, the high frequency waveform is defined to correspond to high frequency physiologic neural oscillations associated with the brain tissue of interest, while the low frequency waveform is defined to correspond to low frequency physiologic neural oscillations associated with the brain tissue of interest. Optionally, one of the carrier and high frequency waveforms may be defined to differ from the low and high frequency physiologic neural oscillations. For example, the high frequency waveform may be defined to correspond to a physiologic beta or gamma wave, while the carrier waveform is defined to be independent of a physiologic deta, theta or alpha wave. Alternatively, the high frequency waveform may be defined to be independent of a physiologic beta or gamma wave, while the carrier waveform is defined to correspond to a physiologic deta, theta or alpha wave.

The carrier wave 820 may represent a non-sinusoidal waveform similar to a square wave, but with only positive or only negative wave segments 822. In the example of FIG. 8A, the carrier wave 820 includes a series of positive wave segments 822 that are defined by parameters, such as a predetermined amplitude 824, segment width 826, inter segment delay 828, among other parameters. The segment width 826 corresponds to the burst length 816, while the inter segment delay 828 corresponds to the interburst delay 808. The segment amplitude 824 defines an average amplitude for each pulse burst 804.

The high-frequency waveform 830 includes a series of bursts 832. Within each burst 832, the waveform 830 oscillates periodically by switching between positive and negative amplitudes 834 and 835 at a select frequency 838. The high-frequency waveform 830 represents an intermittent waveform in that successive adjacent bursts 832 are separated by an interburst delay 836 which corresponds to the interburst delay 808 and inter segment delay 828. The high-frequency waveform 830 is defined by various parameters such as the frequency 138, amplitudes 834, 835, interburst delay 836.

The high-frequency waveform 830 is combined with the carrier waveform 820 to form the nested stimulation waveform 802. The parameters of the high-frequency and carrier waveforms 830 and 820 may be adjusted to achieve various effects. As one example, the parameters may be adjusted to achieve cross frequency coupling with neural oscillations of interest. As one example, the parameters may be adjusted to entrain neural oscillations of interest. For example, the frequency, phase and amplitude of the carrier waveform 820 may be managed to entrain neural oscillations associated with brain tissue of interest, such as tissue associated with sensory, motor or cognitive processing. The carrier waveform 820 may entrain neural oscillations to the temporal structure defined by the carrier waveform 820 such as to facilitate selective attention in connection with certain psychiatric disorders (e.g. schizophrenia, dyslexia, attention deficit/hyperactivity disorder). Additionally or alternatively, the high-frequency waveform 830 may be managed to entrain neural oscillations associated with the brain region of interest. For example, the frequency, phase, amplitude as well as other parameters may be adjusted for the high-frequency waveform 830 to obtain entrainment of the neural oscillations of interest.

The characteristics discussed herein in connection with FIG. 8A represent non-limiting examples of therapy parameters that may be varied to define different nested therapies (e.g., different carrier waveforms and different high frequency waveforms). For example, a non-limiting list of potential therapy parameters include pulse amplitude, pulse frequency, pulse to pulse period, the number of pulses in each burst, burst length, interburst delay, the number of pulse bursts in each nested stimulation waveform and the like. The pulse bursts may include pulses having a frequency corresponding to high frequency intrinsic neural oscillations exhibited by normal/physiologic brain tissue of interest. The pulse bursts are separated from one another with a burst to burst period that corresponds to a frequency of the low-frequency intrinsic neural oscillations exhibited by normal/physiologic brain tissue of interest.

The nested stimulation waveform combines the carrier waveform and high frequency waveform in a predetermined manner. For example, the carrier and high-frequency waveforms may be combined utilizing one of the following types of cross frequency coupling: power to power; phase to power; phase to phase; phase to frequency; power to frequency and frequency to frequency. Optionally, the carrier and high-frequency waveforms are combined through phase to power cross frequency coupling, in which the phase of the carrier waveform modulates the power of the high-frequency waveform. For example, the waveforms 820 and 830 may be combined in the manners discussed herein in connection with FIG. 4.

As one example, first parameters may be set to define the carrier waveform to correspond to physiologic neural oscillations in the theta wave frequency band, while second parameters may be set to define the high-frequency waveform to correspond to physiologic neural oscillations in the gamma wave frequency band. As explained herein, the nested stimulation waveform may be defined to entrain and modulate the neural oscillations in the gamma wave frequency band in connection with at least one of sensory, motor, and cognitive events. Optionally, the nested stimulation waveform may be managed in connection with a patter of interest in neural oscillations through cross frequency coupling between theta and gamma waves associated with the brain tissue of interest.

As explained herein, the brain tissue of interest may correspond to one brain region or comprise distributed neural modules located in separate regions of the brain. In accordance with embodiments herein methods and systems may manage the nested stimulation waveform in connection with cross frequency coupling between neural oscillations associated with one or distributed neural modules that exhibit long-distance communication over neural oscillations within at least one of delta, theta and alpha wave frequency bands.

In accordance with embodiments herein, methods and system measure intrinsic neural oscillations, determine whether the nested stimulation waveform is achieving a desired modulation (e.g., entrainment) of the intrinsic neural oscillations, and adjust at least one of the first and second parameters to maintain the desired modulation (e.g., entrainment) of the intrinsic neural oscillations. The intrinsic neural oscillations may exhibit pathologic behavior or patterns. The nested stimulation waveform is adjusted until the intrinsic neural oscillation exhibits a physiologic behavior or pattern.

Optionally, the nested stimulation waveform may be comprised of more than two waveform components. For example, a hierarchy of nested waveform components may be generated, such as with a base or carrier waveform component, an intermediate waveform component and a high-frequency waveform component. By way of example only, the base waveform component may defined to correspond to physiologic neural oscillations associated with ultra-slow waves, delta waves, theta waves and the like. The intermediate waveform component may be defined to correspond to physiologic neural oscillations associated with theta waves, alpha waves, beta waves, gamma waves and the like. The high-frequency waveform component may be defined correspond to physiologic neural oscillations associated with beta waves, gamma waves, sigma waves and ultrafast waves. Optionally, more than three waveform components may be combined within a nested hierarchy.

As one example, different carrier waveforms may be used based on the location at which the nested stimulation is delivered. For example, the carrier waveform may vary based on whether the stimulation site for tissue of interest represents brain tissue, peripheral neuronal tissue and/or central neuronal tissue. Neuronal tissue includes any tissue associated with the peripheral nervous system or the central nervous system. Peripheral neuronal tissue can include a nerve root or root ganglion or any neuronal tissue that lies outside the brain, brainstem or spinal cord.

Optionally, the nested stimulation waveform may be comprised of waveform components associated with waves or frequency bands that are separated from one another, along the frequency spectrum, in a non-adjacent manner. For example, the waveform components may correspond to frequency ranges that are distributed in a non-successive manner. For example, the carrier waveform component may correspond to neural oscillations in the delta wave range, while the high-frequency waveform component corresponds to neural oscillations in the beta or gamma range. As another example, the carrier waveform component may correspond to neural oscillations in the theta wave range, while the high-frequency waveform component corresponds to neural oscillations in the beta, gamma or ultrafast wave ranges.

While the primary examples provided herein are described in connection with carrier waveforms associated with the delta and theta wave ranges, it is understood that the carrier waveform component may correspond to neural oscillations in higher wave ranges. For example, the carrier waveform component may correspond to neural oscillations in the beta, gamma and even the higher ultrafast wave ranges. By way of example only, it may be desirable to utilize carrier waveform components within the higher range of us in connection with stimulation along the spinal cord and/or dorsal root ganglion.

Optionally, more than one carrier wave component may be included in a nested stimulation waveform.

FIG. 8B illustrates an example of a nested stimulation waveform that may be delivered in connection with nested therapies to brain tissue (or brain tissue) of interest in accordance with embodiments herein. In FIG. 8B, the nested stimulation waveform 842 includes multiple pulse bursts 844 that are separated from one another by an inter-burst delay 848. Each of the pulse burst 844 includes a series of individual pulses or spikes 850. The pulses 850 are delivered over a burst length 856 in connection with an individual pulse burst 844. The rate at which the individual pulses 850 are delivered within a pulse burst 844 is determined based on a pulse rate 862 (denoted as a bracket extending between successive positive peaks of adjacent successive pulses 810. The nested stimulation waveform 842 includes a low frequency carrier waveform 853 and a high frequency waveform that defines the characteristics of the pulses 850.

Figure 8C:
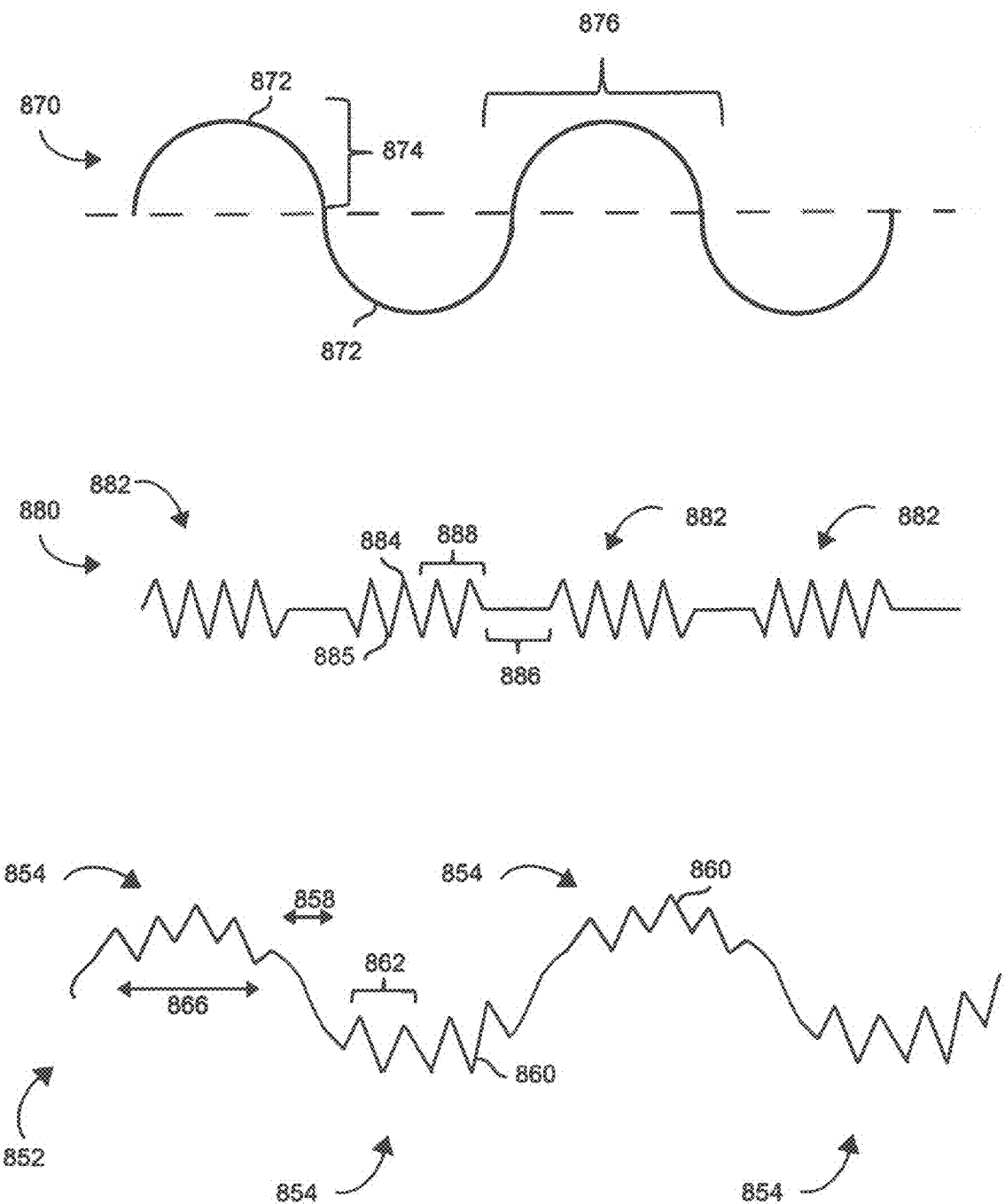
FIG. 8C illustrates an alternative example of a nested stimulation waveform that may be delivered in connection with nested therapies to brain tissue (or brain tissue) of interest in accordance with embodiments herein.

FIG. 8C illustrates an alternative example of a nested stimulation waveform that may be delivered in connection with nested therapies to brain tissue (or brain tissue) of interest in accordance with embodiments herein. In FIG. 8C, the nested stimulation waveform 852 includes multiple pulse bursts 854 that are separated from one another by an inter-burst delay 858. Each of the pulse burst 854 includes a series of individual pulses or spikes 860. The pulses 810 are delivered over a burst length 866 in connection with an individual pulse burst 854. The rate at which the individual pulses 860 are delivered within a pulse burst 854 is determined based on a pulse rate 862 (denoted as a bracket extending between successive positive peaks of adjacent successive pulses 860).

The nested stimulation waveform 852 is decomposed into a carrier waveform 870 and a high-frequency waveform 880. The carrier wave 870 may represent a sinusoidal waveform having positive and negative wave segments 872. The positive and negative wave segments 822 are defined by a predetermined amplitude 874 and segment width 876 among other parameters.

The high-frequency waveform 880 includes a series of bursts 882. Within each burst 882, the waveform 880 oscillates periodically by switching between positive and negative amplitudes 884 and 885 at a select frequency 888. The high-frequency waveform 880 represents an intermittent waveform in that successive adjacent bursts 882 are separated by an interburst delay 886 which corresponds to the interburst delay 858.

The high-frequency waveform 880 is combined with the carrier waveform 870 to form the nested stimulation waveform 852. The parameters of the high-frequency and carrier waveforms 880 and 870 are adjusted to entrain and/or achieve cross frequency coupling with neural oscillations of interest. For example, the frequency, phase and amplitude of the carrier waveform 870 may be managed to entrain neural oscillations associated with a brain region of interest, such as a brain region associated with sensory, motor or cognitive processing. The carrier waveform 870 may entrain neural oscillations to the temporal structure defined by the carrier waveform 870 such as to facilitate selective attention in connection with certain psychiatric disorders (e.g. schizophrenia, dyslexia, attention deficit/hyperactivity disorder). Additionally or alternatively, the high-frequency waveform 880 may be managed to entrain neural oscillations associated with the brain region of interest. For example, the frequency, phase, amplitude as well as other parameters may be adjusted for the high-frequency waveform 880 to obtain entrainment of the neural oscillations of interest.

The carrier and high-frequency waveforms 870 and 880 may be combined utilizing one of the following types of cross frequency coupling: power to power; phase to power; phase to phase; phase to frequency; power to frequency and frequency to frequency. For example, the waveforms 870 and 880 may be combined in the manner discussed herein in connection with FIG. 4. As one example, the carrier and high-frequency waveforms 870 and 880 are combined through phase to power cross frequency coupling (as illustrated in connection with the waveform 405 in FIG. 4), in which the phase of the carrier waveform modulates the power of the high-frequency waveform.

Figure 9:
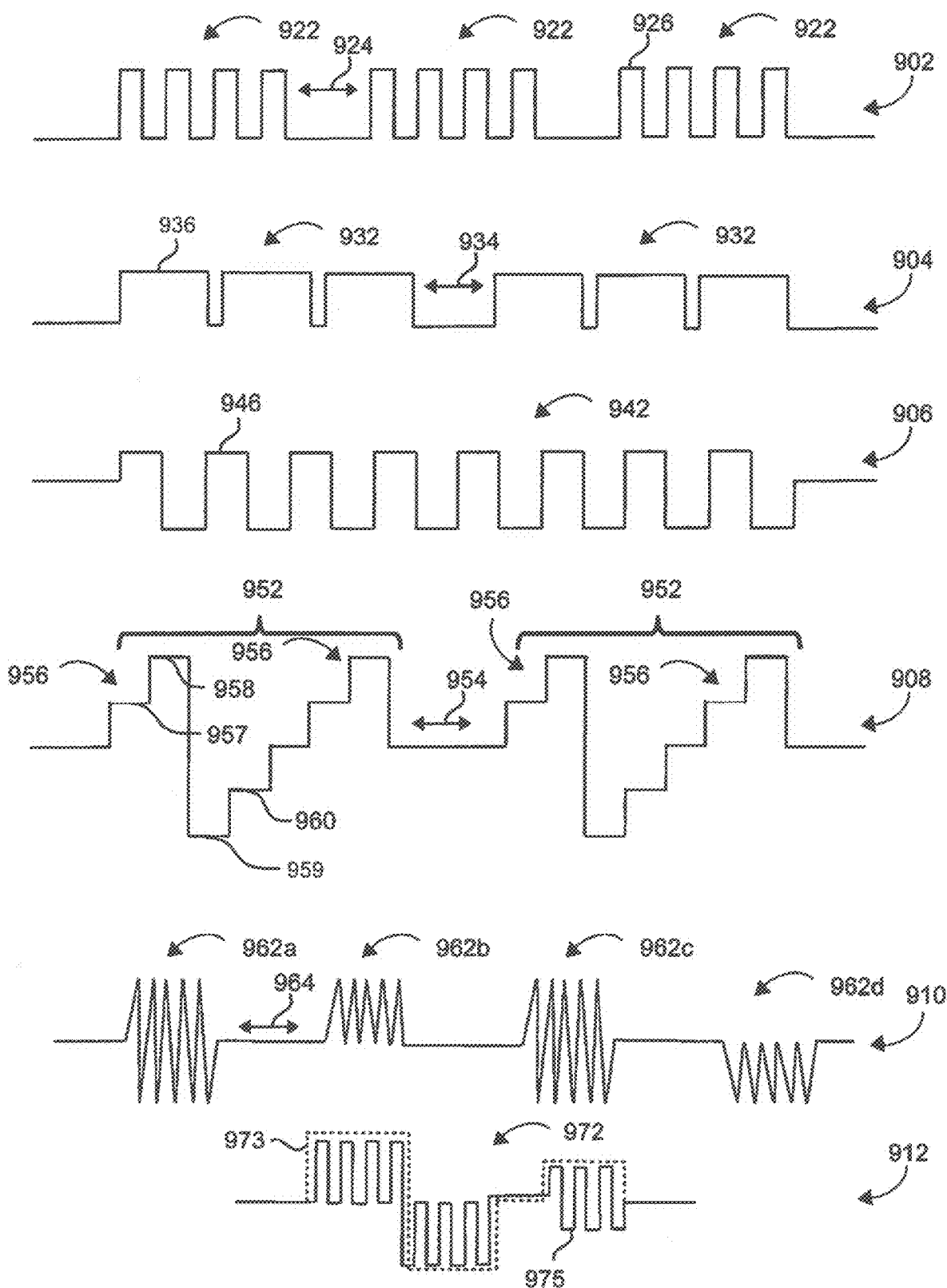
FIG. 9 illustrates alternative nested stimulation waveforms that may be utilized in accordance with embodiments herein.

FIG. 9 illustrates alternative nested stimulation waveforms that may be utilized in accordance with embodiments herein. The nested stimulation waveforms 902-912 may be delivered from multiple electrode combinations along the lead. The nested stimulation waveform 902 includes a carrier waveform that is cross frequency coupled to a high frequency waveform to form multiple (e.g. three) pulse bursts 922 separated by an inter-burst interval 924. The pulse burst 922 include a series of pulses 926 having a common polarity (e.g. all positive pulses or all negative pulses).

The nested stimulation waveform 904 includes a pair of pulse bursts 932 separated by an interburst interval 934. Each pulse burst 932 includes a series of pulses 936 (e.g. three) that have a common polarity. The nested stimulation waveform 906 includes a single pulse burst 942 having a series of pulses 946, each of which is bipolar (e.g. extends between positive and negative polarities). The pulses 946 have one of two states/voltage levels, namely a positive pulse amplitude and a negative pulse amplitude that are common.

The stimulation waveform 908 includes a pair of pulse bursts 952 separated by an inter-burst interval 954. Each pulse burst 952 includes multiple pulses 956 that are bipolar (extending between positive and negative polarities). The pulses 956 vary between more than two states or voltage levels, namely first and second positive voltages 957-958 and first and second negative voltages 959 and 960. Optionally, additional voltage levels/states may be utilized and the positive and negative voltage levels need not be common.

The nested stimulation waveform 910 includes pulse burst 962A-962D that are separated by an interburst interval 964. The interburst intervals 964 may differ from one another or be common. The pulse bursts 962A and 962C have similar positive and negative amplitudes, while the pulse bursts 962B (positive) and 962D (negative) are monopolar and different from one another. The nested stimulation waveform 912 illustrates a single pulse burst 972 that has a carrier wave component (as denoted by envelope 973 in dashed lines) that is modulated by a higher frequency component (as denoted by solid lines 975). Optionally, the nested stimulation waveform may be varied from the foregoing examples. Additionally, separate and distinct nested stimulation waveforms may be delivered from different electrode combinations at non-overlapping distinct points in time.

Figure 10:
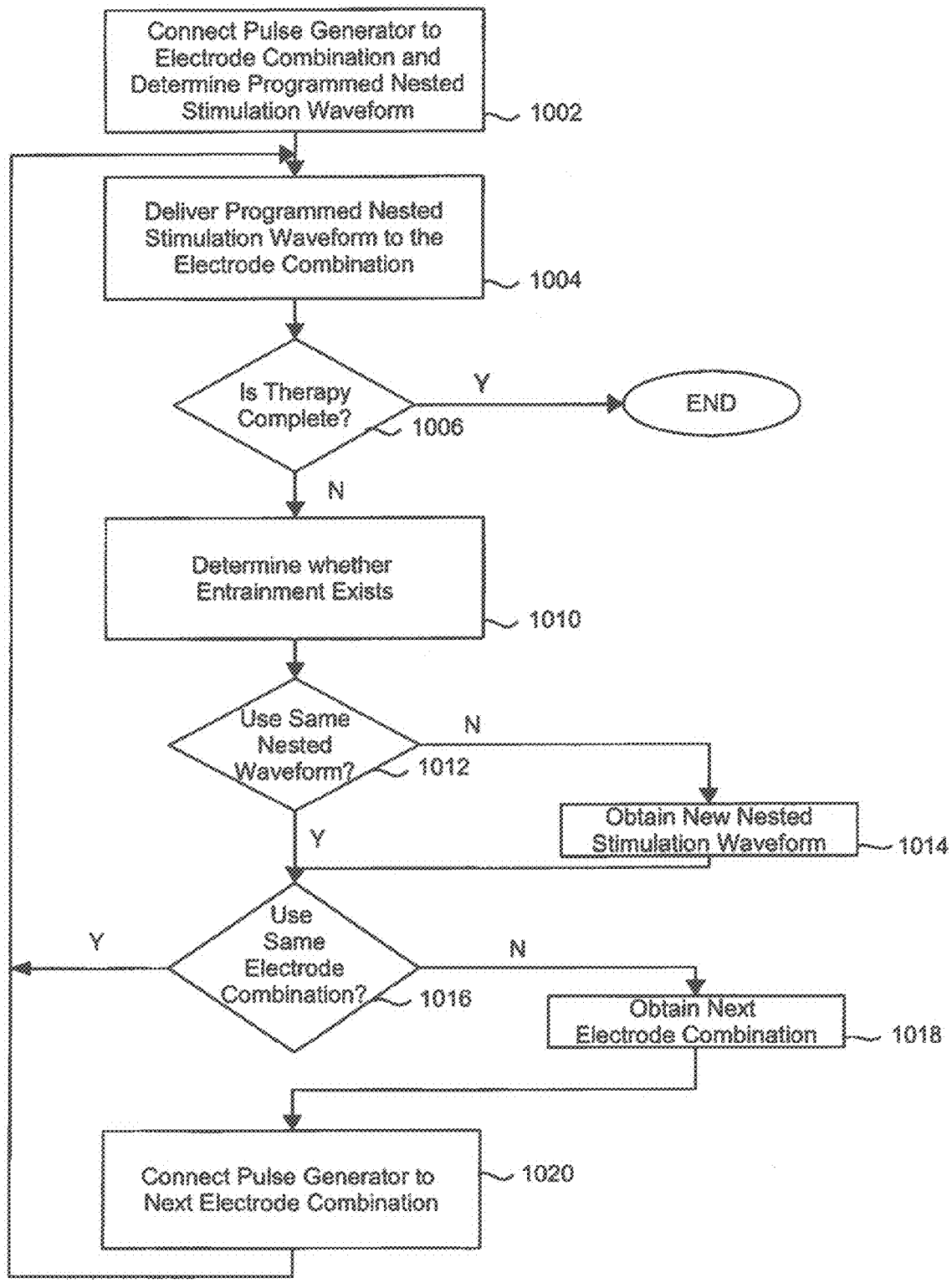
FIG. 10 illustrates a process for managing delivery of nested stimulation waveforms to tissue of interest in accordance with embodiments herein.

FIG. 10 illustrates a process for managing delivery of nested stimulation waveforms to tissue of interest in accordance with embodiments herein. The operations of FIG. 10 may be implemented by one or more processors, such as within an implantable medical device, external programmer, another external device and the like. The IMD, external programmer or other external device are coupled to a lead having at least one stimulation electrode that is implanted at a target position proximate to nervous tissue of interest.

At 1002, the IMD (processor) manages a switch circuit therein to connect the pulse generator to a select electrode combination as defined by a programmed therapy parameter set. At 1002, the IMD also determines the nested stimulation waveform to be utilized. The stimulation waveform is defined by one or more parameters forming a therapy parameter set (TPS). The IMD (processor) manages the pulse generator in the IMD to generate the nested stimulation waveform by combining predetermined carrier and high frequency waveforms. Examples of parameters within a TPS include, but are not limited to pulse amplitude, pulse width, interpulse delay, number of pulses per burst, pulse frequency, burst frequency, burst to burst frequency, pulse frequency, burst length and burst period for the plurality of pulse bursts. Other examples are discussed herein.

At 1004, the IMD delivers a nested stimulation waveform to the select electrode combination within the array of electrodes located proximate to nervous tissue of interest. The stimulation waveform is delivered to at least one stimulation electrode combination on the lead. As contemplated in embodiments herein, a predetermined stimulation site for tissue of interest can include brain tissue, peripheral neuronal tissue and/or central neuronal tissue. Neuronal tissue includes any tissue associated with the peripheral nervous system or the central nervous system. Peripheral neuronal tissue can include a nerve root or root ganglion or any neuronal tissue that lies outside the brain, brainstem or spinal cord. At 1006, the IMD determines whether the therapy is complete. When the therapy is complete, the process ends. Otherwise, the process continues to 1010.

At 1010, the IMD determines whether the nested stimulation waveform continues to have an intended effect (e.g., entrain) on the intrinsic neural oscillations for the tissue of interest. For example, the IMD may determine whether the intrinsic neural oscillations remain in phase with the nested stimulation waveform. When the intrinsic neural oscillations remain entrained (e.g. in phase or at a select phase shift relative to) the nested stimulation waveform, entrainment or another desired effect may be determined to exist. Other characteristics, besides or in addition to phase may be utilized to determine whether the stimulation waveform modifies the neural oscillations in a desired manner. For example, the IMD may measure intrinsic neural oscillations and determine whether the nested stimulation waveform is achieving entrainment of the intrinsic neural oscillations.

At 1012, the IMD (processor) determines whether to adjust at least one of the first and second parameters to maintain entrainment of the intrinsic neural oscillations. The IMD determines whether to use the same nested stimulation waveform or to use a different nested stimulation waveform and/or exhibits a desired frequency, amplitude, etc. For example, when entrainment continues to occur at 1010, it may be desirable to continue to apply the same nested stimulation waveform. Alternatively, when, at 1010, it is determined that the nested stimulation waveform is not achieving entrainment (or has lost entrainment), it may be desirable to change the nested stimulation waveform. A change in the nested stimulation waveform may be very minor, such as a slight phase shift. Alternatively or in addition, the change in the stimulation waveform may be substantial. The nested stimulation waveform may change one or more characteristics, such as the frequency of the carrier waveform, the frequency of the high-frequency component, as well as other parameters described herein. Additionally or alternatively, the form of cross frequency coupling may be changes. For example, in one iteration through the operations of FIG. 10, the carrier and high frequency waveforms may be combined utilizing phase to power cross frequency coupling. However, at 1010, it may be determined that the nested stimulation waveform is not achieving a desired result (e.g., entrainment). Consequently, at 1012, it may be determined to change (at 1014) the nested stimulation waveform by changing the type of cross frequency coupling, such as to switch from phase to phase or power to power coupling.

When the same waveform is to be utilized, flow moves to 1016. Otherwise, flow advances to 1014. At 1014, the IMD obtains the next or successive nested stimulation waveform to be utilized. Thereafter, flow moves to 1016. At 1016, the IMD (processor) determines whether to use the same electrode combination as with the prior cycle. If so, flow returns to 1004. Otherwise, flow advances to 1018. At 1018, the IMD obtains the next electrode combination to be utilized. At 1020, the IMD manages the switch to connect the pulse generator to the corresponding next electrode combination. Thereafter, flow returns to 1004 where the next nested stimulation waveform is delivered.

The operations of FIG. 10 are continuously repeated indefinitely, periodically or for a select period of time. In accordance with the foregoing manner, the IMD sequentially delivering (through the operations at 1004-1020) successive nested stimulation waveforms to successive electrode combinations within the array of electrodes, the first and successive nested stimulation waveforms including at least one series of pulses having a pulse amplitude and pulse frequency. The IMD delays delivery of the successive nested stimulation waveforms by the entrainment delay at 1010. The IMD manages at least one of the therapy parameters of the first and successive nested stimulation waveforms to excite the nervous tissue of interest.

In the foregoing process of FIG. 10, the IMD operates in accordance with the preprogrammed therapy parameter set that is defined by a physician, clinician, the patient or otherwise. The therapy parameter set may be determined in various manners, such as based upon data collected from numerous studies, prior patients, a present patient over time and the like.

Figure 11:
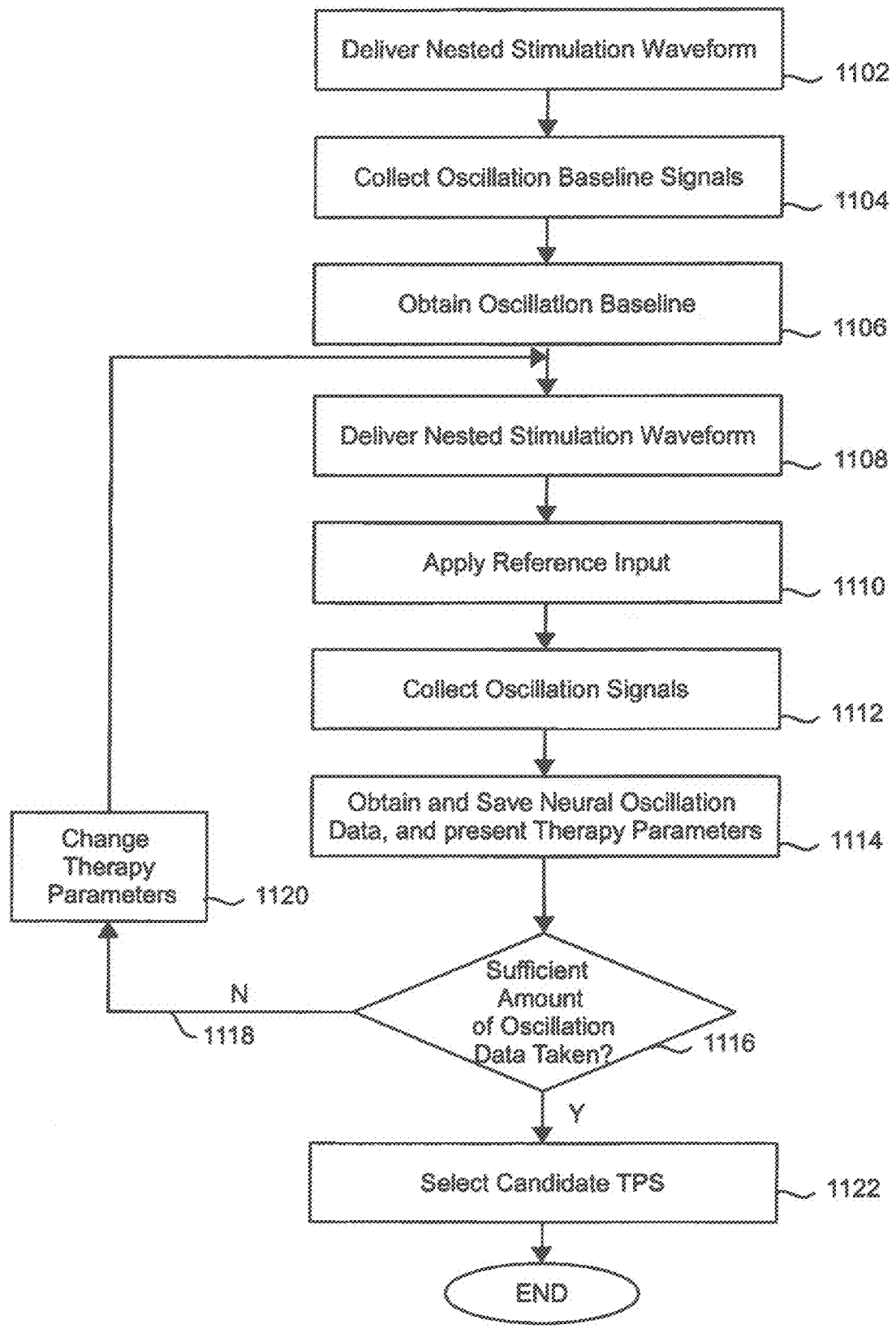
FIG. 11 illustrates a process for collecting and analyzing neural oscillations in connection with identifying desired nested stimulation waveforms in accordance with embodiments herein.

FIG. 11 illustrates a process for collecting and analyzing neural oscillations in connection with identifying desired nested stimulation waveforms in accordance with embodiments herein. At 1102, the method defines one or more nested stimulation waveform to be used. The nested stimulation waveform is defined by one or more parameters forming a therapy parameter set (TPS), wherein at least first parameters define a carrier waveform and at least second parameters define a high frequency waveform.

At 1104, the method senses intrinsic neural oscillation baseline signals by collecting neural oscillation signals for a data collection window while baseline conditions are maintained (e.g., no external input is applied to the patient). The oscillation baseline signals are indicative of the brain wave activity exhibited naturally or inherently by brain tissue of interest at one or more target sites. The oscillation baseline signals, collected over a single data collection window, represent an oscillation baseline sample for a single time interval, where the oscillation baseline sample is indicative of a baseline oscillation pattern generated by the brain tissue of interest.

Throughout the embodiments described herein, the same electrodes may be used for sensing and stimulation. Alternatively, one group of electrodes may be used for sensing, while a different group of electrodes are used for stimulation. For example, the sensing electrodes may be spaced apart along the lead from the stimulation electrodes. Optionally, the sensing electrodes may be provided on a separate lead unique and distinct from the lead that includes the stimulation electrodes. In various embodiments herein, electrodes and leads may be used for stimulation and/or sensing, provided that the electrodes are configured to be located at a desired proximity relative to a target site or tissue of interest. Additionally or alternatively, the lead to be used for sensing may include micro electrodes (alone or in combination with conventional electrodes), where the micro electrodes that are configured to be placed immediately adjacent brain tissue of interest.

At 1106, the oscillation baseline signal is analyzed to define baseline features within the morphology of the oscillation signal. By way of example, the oscillation baseline signals may be processed through a fast Fourier transform to separate the frequency components therein. The frequency components within a frequency band of interest (e.g. the band associated with the delta, theta, alpha, beta or gamma waves) are analyzed to define one or more parameters of interest associated with the morphology of the frequency band of interest.

For example, the baseline features may represent the phase, frequency and amplitude of the neural oscillations collected in the beta wave frequency range. Additionally or alternatively, the baseline features may represent the phase, frequency and amplitude of the neural oscillations within the delta wave frequency range. As another example, the baseline features may represent an amplitude of peaks, a number of peaks, a number of direction changes and the like within the baseline sample collected over the data collection window. The baseline sample(s) and their features described above are stored in memory. The baseline samples may be used over time as a reference such as in connection with defining a nested stimulation therapy, and/or for comparison with later collected baseline samples, such as to determine when a patient's inherent level of oscillation activity is increasing or decreasing. Optionally, the operations at 1104 and 1106 may be omitted entirely.

At 1108, the method delivers the nested stimulation waveform to at least one electrode based on the TPS defined at 1102. The stimulation waveform is delivered to at least one stimulation electrode on the lead. At 1110, the method applies a predetermined external sensory stimulation that is configured to induce select neural oscillation patterns within the brain tissue of interest. The reference input may represent a predetermined degree or amount of touch. Optionally, the reference input may correspond to the patient speaking, viewing a picture, holding an object, performing a physical motion, or any other external input intended to otherwise cause the select neural oscillation pattern. Optionally, the reference input may correspond to the patient undergoing a recognition or memory exercise. The reference input is applied in a repeatable manner and may be applied repeatedly at different times while intrinsic neural oscillation signals are collected in connection with different TPS.

At 1112, the method senses neural oscillation signals and collects the neural oscillation signals for a data collection window. The neural oscillation signals are indicative of the brain wave activity exhibited by nervous tissue of interest at the target position in response to the reference or noxious input. The neural oscillation signals, collected over a single data collection window, represent an oscillation sample for a single time interval, where the oscillation sample is indicative of a responsiveness of the fibers of interest when a predetermined external sensory stimulation is delivered. The neural oscillation signals are saved as an oscillation sample.

At 1114, the method analyzes the neural oscillation signal (e.g., the oscillation sample) to obtain neural oscillation data associated with the TPS. The neural oscillation data corresponds to brain wave activity for the tissue of interest. The analysis at 1114 is repeated numerous times to obtain a collection of neural oscillation data associated with a group or multiple TPS. In the embodiment illustrated in FIG. 11, the operation at 1114 may be implemented during each iteration through the operation at 1108-1120. At 1114, the method also saves the neural oscillation data along with the values for the corresponding therapy parameter set, such as in a memory of the IPG, external programmer or other external device. The neural oscillation data and the associated therapy parameter set are saved, over time, in connection with delivering therapy based on multiple therapy parameter sets, thereby developing a therapy/oscillatory interaction history for the patient.

At 1116, the method determines whether a sufficient number of oscillation samples have been collected (and analyzed). When a sufficient number of oscillation samples have been collected, flow moves to 1122. When it is determined that additional oscillation samples should be collected, flow moves along 1118 to 1120. At 1120, the method changes a value for one or more of the parameters within the therapy parameter set. The change at 1120 may be performed in a predetermined systematic stepwise manner. For example, each parameter within the therapy parameter set may be incrementally adjusted by a select amount during separate iterations through the operations at 1108-1116. As an example, during iterations 1-11, the method may only change the amplitude of the stimulation waveform between low, medium and high amplitudes, while maintaining constant all other parameters within the TPS. After cycling through each of the pulse amplitudes of interest, the pulse amplitude may be reset to the low level for iterations 4-6, during which the pulse width is changed from short to medium to long. During iterations 7-9, the pulse amplitude may be set to the medium level, while the pulse width is again changed from short to medium to long, while all other parameters are maintained constant. The foregoing process may be repeated until each, or at least a select portion, of the potential permutations and combinations of levels for the parameters are used during the operations at 1108-1116 to form the group of TPS for which the collection of neural oscillations is accumulated.

Alternatively or additionally, not all permutations and combinations of parameter levels may be used. For example, a physician or other user may select (and/or program) individual TPS of interest to be tested as the group of TPS. For example, the operations at 1108-1116 may only be repeated for 5 to 10 or 20 different TPS, even though many more permutations and combinations of levels for the various parameters exist. The change performed at 1120 may be based on pre-stored settings or may represent an input from a physician or other user during operation.

Optionally, the amount of change during each iteration through 1120 may vary, such as with larger step changes made during initial iterations and smaller step changes made during later iterations. Optionally, the amount of change at 1120 may be based on a difference between the neural oscillations and the threshold. For example, when the neural oscillations substantially exceeds the threshold, larger changes may be applied to one or more parameters at 1120. As the difference between the neural oscillations and threshold decreases, the incremental change in the one or more parameters is changed by similarly/proportionally decreasing amounts. Following 1120, flow returns to 1108.

At 1122, the method selects a candidate TPS from the multiple or group of TPS based on one or more criteria of interest. For example, when the criteria of interest represents a threshold or predetermined range for the neural oscillations, the candidate TPS may be selected as the TPS that resulted in neural oscillations that satisfy the threshold or predetermined range. For example, when the criteria of interest represents sensory activity, at 1122, the method may identify the oscillation sample for which the lowest or smallest amount of neural oscillations was identified. The lowest or smallest amount of activity is measured relative to the neural oscillations of the other oscillation samples. The method cross references oscillation sample, that exhibits the lowest or smallest amount of neural oscillations, to the corresponding therapy parameter set which is designated as the candidate TPS. As one example, the selection at 1122 may seek to optimize the candidate TPS to define as a burst stimulation waveform that affords an oscillation activity below a threshold or within a range, collectively referred to as a result of interest, without inducing paresthesia. Once a candidate TPS is selected, the candidate TPS is used for subsequent therapy for a period of time, for example until it becomes desirable to repeat the process of FIG. 11 to determine a new candidate TPS.

Figure 12:
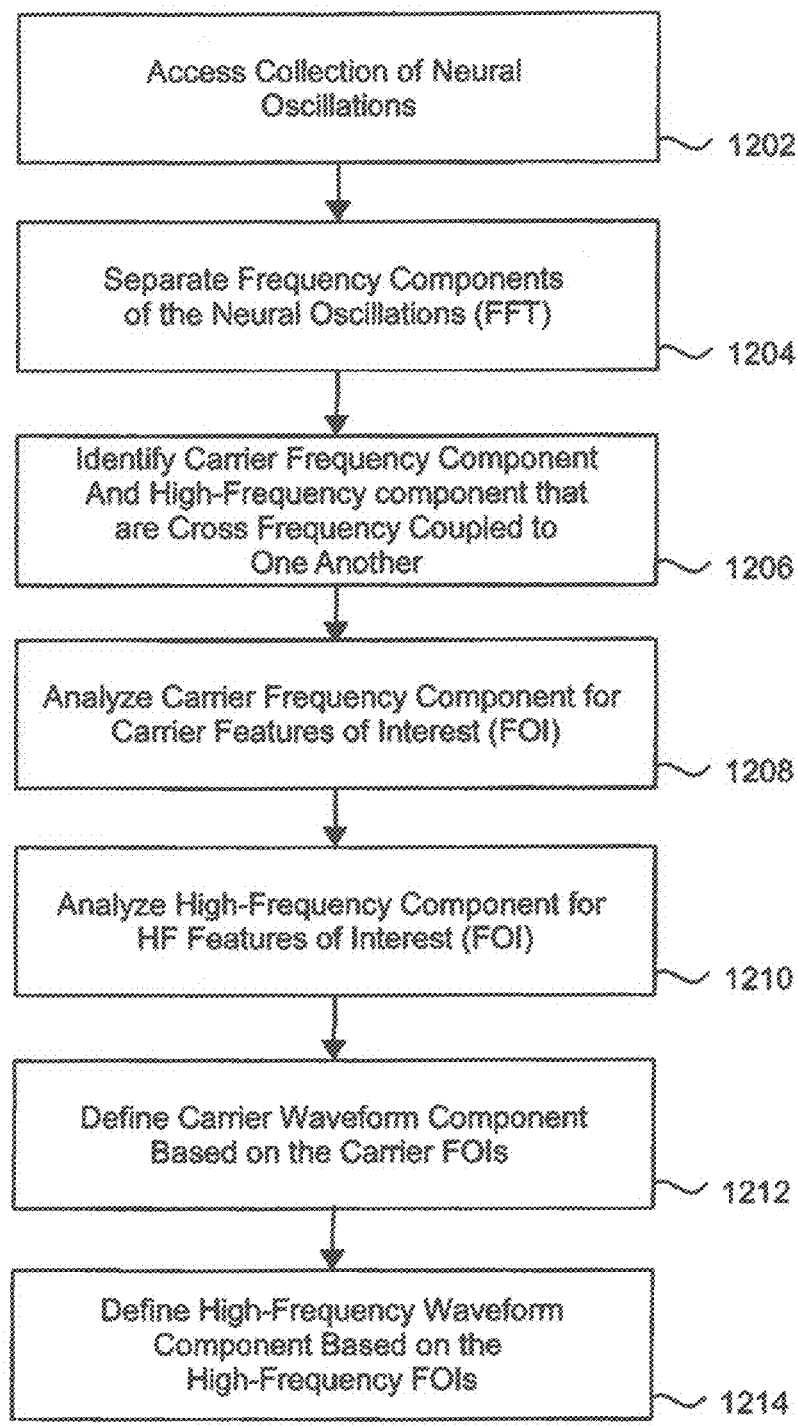
FIG. 12 illustrates a process for defining a nested stimulation waveform based on neural oscillations in accordance with embodiments herein.

FIG. 12 illustrates a process for defining a nested stimulation waveform based on neural oscillations in accordance with embodiments herein. At 1202, a collection of intrinsic neural oscillations is obtained. For example, the collection of intrinsic neural oscillations may be prerecorded from a collection of patients, prerecorded at multiple points in time from an individual patient, or recorded during a surgical operation in which a system as described herein is being implanted.

At 1204, the neural oscillations are processed by a processor to separate the frequency components of interest therein. For example, the neural oscillations may be passed through a fast Fourier transform and one or more bandpass filters to separate the various frequency components associated with each type of brain wave activity of interest. As noted in connection with FIG. 3, separate frequency ranges exist for delta waves, theta waves, alpha waves, beta waves and gamma waves. A separate bandpass filter may be shaped by the processor to isolate each of the brain wave frequency ranges.

At 1206, the processor identifies a carrier frequency component and a high frequency component of interest that are cross frequency coupled to one another. For example, the delta wave frequency component may be identified as the carrier frequency component, while the theta or alpha wave frequency component is identified as the high-frequency component. As another example, the theta wave frequency component may be identified as the carrier frequency component while the beta or gamma wave frequency components are identified as the high-frequency component.

At 1208, the processor analyzes the carrier frequency component for features of interest (e.g. phase, frequency, amplitude). At 1210, the process analyzes the high-frequency component for one or more features of interest. At 1212, the processor defines a carrier waveform component to be used in connection with generating a nested stimulation waveform based on the carrier FOIs. At 1214, the process defines a high-frequency waveform component to be used in connection with generating the nested stimulation waveform based on the high-frequency FOIs.

The operations of FIG. 12 may be repeated numerous times in connection with different collections of oscillation signals to define multiple therapy parameter sets used in connection with generating different types of nested stimulation waveforms. For example, the therapy parameter sets may identify numerous types of carrier waveform components, as well as numerous types of high-frequency waveform components, such as illustrated in FIGS. 8A-8C and 9.

The operations of FIG. 12 may be carried out by one or more processors of the IMD, an external device, or otherwise.

Electrical Stimulation Devices

Figure 1B:
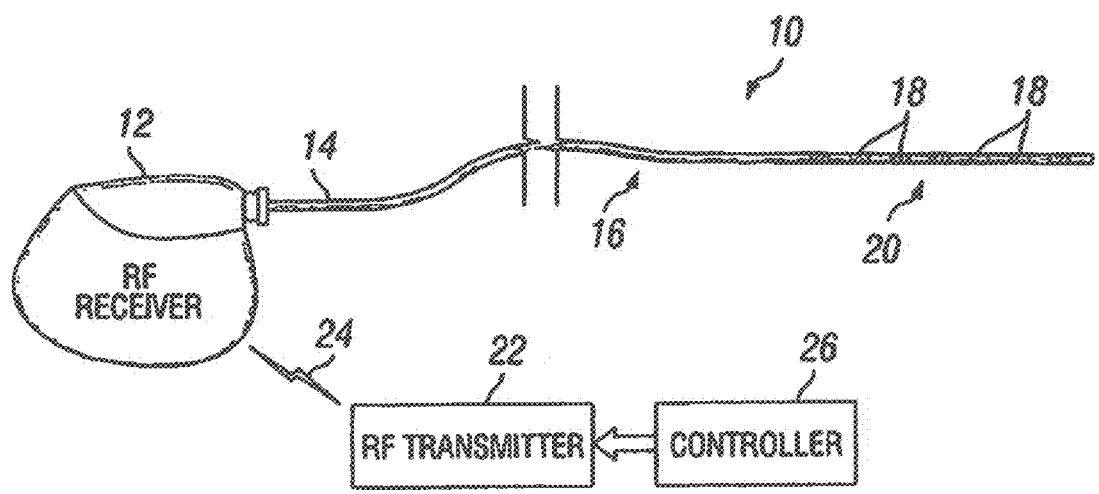
FIG. 1B illustrates an example neurological stimulation (NS) systems for electrically stimulating a predetermined site area to treat one or more neurological disorders or conditions in accordance with embodiments herein.

FIGS. 1A-1B illustrate example neurological stimulation (NS) systems 10 for electrically stimulating a predetermined site area to treat one or more neurological disorders or conditions. In general terms, stimulation system 10 includes an implantable pulse generating source or electrical IMD 12 (generally referred to as an "implantable medical device" or "IMD") and one or more implantable electrodes or electrical stimulation leads 14 for applying nested stimulation pulses to a predetermined site. In operation, both of these primary components are implanted in the person's body, as discussed below. In certain embodiments, IMD 12 is coupled directly to a connecting portion 16 of stimulation lead 14. In other embodiments, IMD 12 is incorporated into the stimulation lead 14 and IMD 12 instead is embedded within stimulation lead 14. For example, such a stimulation system 10 may be a Bion® stimulation system manufactured by Advanced Bionics Corporation. Whether IMD 12 is coupled directly to or embedded within the stimulation lead 14, IMD 12 controls the stimulation pulses transmitted to one or more stimulation electrodes 18 located on a stimulating portion 20 of stimulation lead 14, positioned in communication with a predetermined site, according to suitable therapy parameters (e.g., duration, amplitude or intensity, frequency, pulse width, firing delay, etc.).

As contemplated in embodiments herein, a predetermined stimulation site for tissue of interest can include either peripheral neuronal tissue and/or central neuronal tissue.

Neuronal tissue includes any tissue associated with the peripheral nervous system or the central nervous system. Peripheral neuronal tissue can include a nerve root or root ganglion or any neuronal tissue that lies outside the brain, brainstem or spinal cord. Peripheral nerves can include, but are not limited to olfactory nerve, optic, nerve, oculomotor nerve, trochlear nerve, trigeminal nerve, abducens nerve, facial nerve, vestibulocochlear (auditory) nerve, glossopharyngeal nerve, vagal nerve, accessory nerve, hypoglossal nerve, suboccipital nerve, the greater occipital nerve, the lesser occipital nerve, the greater auricular nerve, the lesser auricular nerve, the phrenic nerve, brachial plexus, radial axillary nerves, musculocutaneous nerves, radial nerves, ulnar nerves, median nerves, intercostal nerves, lumbosacral plexus, sciatic nerves, common peroneal nerve, tibial nerves, sural nerves, femoral nerves, gluteal nerves, thoracic spinal nerves, obturator nerves, digital nerves, pudendal nerves, plantar nerves, saphenous nerves, ilioinguinal nerves, gentofemoral nerves, and iliohypogastric nerves.

Central neuronal tissue includes brain tissue, spinal tissue or brainstem tissue. Brain tissue can include thalamus/subthalamus, basal ganglia, hippocampus, amygdala, hypothalamus, mammilary bodies, substantia nigra or cortex or white matter tracts afferent to or efferent from the above-mentioned brain tissue, inclusive of the corpus callosum. Spinal tissue can include the ascending and descending tracts of the spinal cord, more specifically, the ascending tracts of that comprise intralaminar neurons or the dorsal column. The brainstem tissue can include the medulla oblongata, pons or mesencephalon, more particular the posterior pons or posterior mesencephalon, Lushka's foramen, and ventrolateral part of the medulla oblongata.

A doctor, the patient, or another user of IMD 12 may directly or in directly input therapy parameters to specify or modify the nature of the stimulation provided.

In FIG. 1B, the IMD 12 includes an implantable wireless receiver. An example of a wireless receiver may be one manufactured by Advanced Neuromodulation Systems, Inc., such as the Renew® System, part numbers 3408 and 3416. In another embodiment, the IMD can be optimized for high frequency operation as described in U.S. Provisional Application Ser. No. 60/685,036, filed May 26, 2005, entitled "SYSTEMS AND METHODS FOR USE IN PULSE GENERATION," which is incorporated herein by reference. The wireless receiver is capable of receiving wireless signals from a wireless transmitter 22 located external to the person's body. The wireless signals are represented in FIG. 1B by wireless link symbol 24. A doctor, the patient, or another user of IMD 12 may use a controller 26 located external to the person's body to provide control signals for operation of IMD 12. Controller 26 provides the control signals to wireless transmitter 22, wireless transmitter 22 transmits the control signals and power to the wireless receiver of IMD 12, and IMD 12 uses the control signals to vary the signal parameters of electrical signals transmitted through electrical stimulation lead 14 to the stimulation site. Thus, the external controller 26 can be for example, a handheld programmer, to provide a means for programming the IMD. An example wireless transmitter may be one manufactured by Advanced Neuromodulation Systems, Inc., such as the Renew® System, part numbers 3508 and 3516.

The IMD 12 applies burst stimulation to brain tissue of a patient. Specifically, the IMD includes a microprocessor and a pulse generation module. The pulse generation module generates the electrical pulses according to a defined pulse width and pulse amplitude and applies the electrical pulses to defined electrodes. The microprocessor controls the operations of the pulse generation module according to software instructions stored in the device.

The IMD 12 can be adapted by programming the microprocessor to deliver a number of spikes (relatively short pulse width pulses) that are separated by an appropriate interspike interval. Thereafter, the programming of the microprocessor causes the pulse generation module to cease pulse generation operations for an interburst interval. The programming of the microprocessor also causes a repetition of the spike generation and cessation of operations for a predetermined number of times. After the predetermined number of repetitions has been completed within a nested stimulation waveform, the microprocessor can cause burst stimulation to cease for an amount of time (and resume thereafter). Also, in some embodiments, the microprocessor could be programmed to cause the pulse generation module to deliver a hyperpolarizing pulse before the first spike of each group of multiple spikes.

The microprocessor can be programmed to allow the various characteristics of the burst stimulus to be set by a physician to allow the burst stimulus to be optimized for a particular pathology of a patient. For example, the spike amplitude, the interspike interval, the interburst interval, the number of bursts to be repeated in succession, the electrode combinations, the firing delay between nested stimulation waveforms delivered to different electrode combinations, the amplitude of the hyperpolarizing pulse, and other such characteristics could be controlled using respective parameters accessed by the microprocessor during burst stimulus operations. These parameters could be set to desired values by an external programming device via wireless communication with the implantable neuromodulation device.

In another embodiment, the IMD 12 can be implemented to apply burst stimulation using a digital signal processor and one or several digital-to-analog converters. The burst stimulus waveform could be defined in memory and applied to the digital-to-analog converter(s) for application through electrodes of the medical lead. The digital signal processor could scale the various portions of the waveform in amplitude and within the time domain (e.g., for the various intervals) according to the various burst parameters.

Figure 1C:
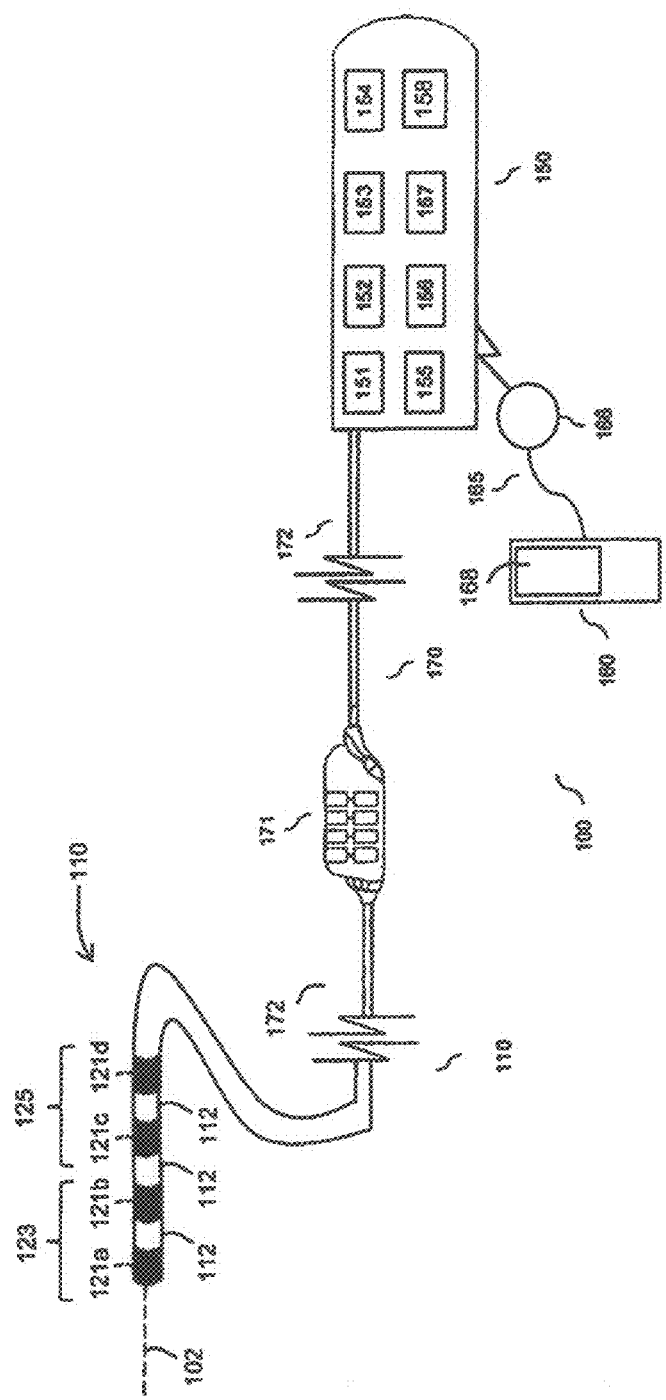
FIG. 1C depicts an NS system that delivers nested therapies in accordance with embodiments herein.
Figure 2A:
FIG. 2A illustrates example stimulation leads that may be used for electrically stimulating the predetermined site to treat one or more neurological disorders or conditions in accordance with embodiments herein.
Figure 2B:
FIG. 2B illustrates example stimulation leads that may be used for electrically stimulating the predetermined site to treat one or more neurological disorders or conditions in accordance with embodiments herein.
Figure 2C:
FIG. 2C illustrates example stimulation leads that may be used for electrically stimulating the predetermined site to treat one or more neurological disorders or conditions in accordance with embodiments herein.
Figure 2D:
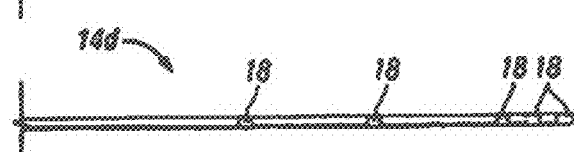
FIG. 2D illustrates example stimulation leads that may be used for electrically stimulating the predetermined site to treat one or more neurological disorders or conditions in accordance with embodiments herein.
Figure 2E:
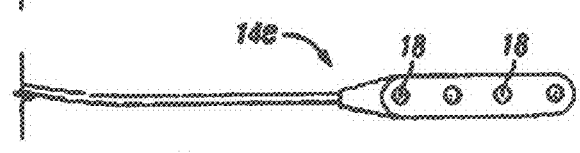
FIG. 2E illustrates example stimulation leads that may be used for electrically stimulating the predetermined site to treat one or more neurological disorders or conditions in accordance with embodiments herein.
Figure 2F:
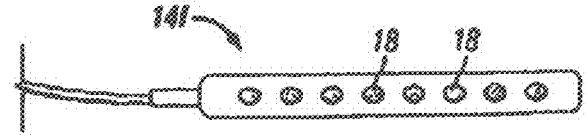
FIG. 2F illustrates example stimulation leads that may be used for electrically stimulating the predetermined site to treat one or more neurological disorders or conditions in accordance with embodiments herein.
Figure 2G:
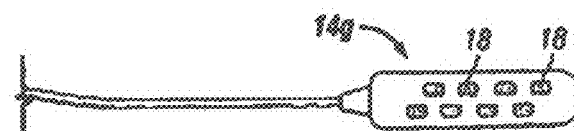
FIG. 2G illustrates example stimulation leads that may be used for electrically stimulating the predetermined site to treat one or more neurological disorders or conditions in accordance with embodiments herein.
Figure 2H:
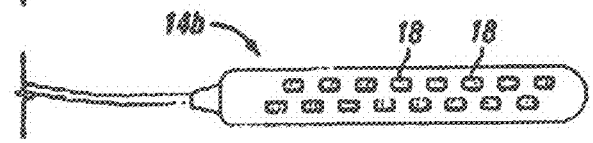
FIG. 2H illustrates example stimulation leads that may be used for electrically stimulating the predetermined site to treat one or more neurological disorders or conditions in accordance with embodiments herein.
Figure 2I:
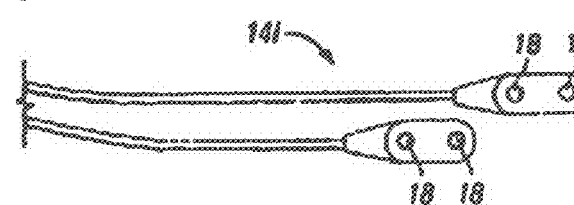
FIG. 2I illustrates example stimulation leads that may be used for electrically stimulating the predetermined site to treat one or more neurological disorders or conditions in accordance with embodiments herein.

FIG. 1C depicts an NS system 100 that delivers nested therapies in accordance with embodiments herein. For example, the NS system 100 may be adapted to stimulate spinal cord tissue, peripheral nervous tissue, deep brain tissue, or any other suitable nervous/brain tissue of interest within a patient's body.

The NS system 100 may be controlled to deliver various types of nested stimulation therapy, such as high frequency neurostimulation therapies, burst neurostimulation therapies and the like. High frequency neurostimulation includes a continuous series of monophasic or biphasic pulses that are delivered at a predetermined frequency. Burst neurostimulation includes short sequences of monophasic or biphasic pulses, where each sequence is separated by a quiescent period. In general, nested therapies include a continuous, repeating or intermittent pulse sequence delivered at a frequency and amplitude configured to avoid inducing (or introduce a very limited) paresthesia.

The NS system 100 may deliver nested stimulation therapy based on preprogrammed therapy parameters. The therapy parameters may include, among other things, pulse amplitude, pulse polarity, pulse width, pulse frequency, interpulse interval, inter burst interval, electrode combinations, firing delay and the like. Optionally, the NS system 100 may represent a closed loop neurostimulation device that is configured to provide real-time sensing functions from a lead. The configuration of the lead sensing electrodes may be varied depending on the neuronal anatomy of the sensing site(s) of interest. The size and shape of electrodes is varied based on the implant location. The electronic components within the NS system 100 are designed with both stimulation and sensing capabilities, including alternative nested stimulation therapy, such as burst mode, high frequency mode and the like.

The NS system 100 includes an implantable medical device (IMD) 150 that is adapted to generate electrical pulses for application to tissue of a patient. The IMD 150 typically comprises a metallic housing or can 158 that encloses a controller 151, pulse generating circuitry 152, a charge storage circuit 153, a battery 154, a far-field and/or near field communication circuitry 155, battery charging circuitry 156, switching circuitry 157, memory 158 and the like. The charge storage circuit 153 may represent one or more capacitors and/or battery cells that store charge used to produce the therapies described herein. The pulse generating circuitry 152, under control of the controller 151, manages discharge of the charge storage circuit 153 to shape the morphology of the waveform delivered while discharging energy. The switching circuitry 157 connects select combinations of the electrodes 121a-d to the pulse generating circuitry 152 thereby directing the stimulation waveform to a desired electrode combination. As explained herein, the switching circuitry 157 successively connects the pulse generating circuitry 152 to successive electrode combinations 123 and 125. The components 151-158 are also within the IMD 12 (FIGS. 1A and 1B).

The controller 151 typically includes one or more processors, such as a microcontroller, for controlling the various other components of the device. Software code is typically stored in memory of the IMD 150 for execution by the microcontroller or processor to control the various components of the device.

The IMD 150 may comprise a separate or an attached extension component 170. If the extension component 170 is a separate component, the extension component 170 may connect with the "header" portion of the IMD 150 as is known in the art. If the extension component 170 is integrated with the IMD 150, internal electrical connections may be made through respective conductive components. Within the IMD 150, electrical pulses are generated by the pulse generating circuitry 152 and are provided to the switching circuitry 157. The switching circuitry 157 connects to outputs of the IMD 150. Electrical connectors (e.g., "Bal-Seal" connectors) within the connector portion 171 of the extension component 170 or within the IMD header may be employed to conduct various stimulation pulses. The terminals of one or more leads 110 are inserted within connector portion 171 or within the IMD header for electrical connection with respective connectors. Thereby, the pulses originating from the IMD 150 are provided to the lead 110. The pulses are then conducted through the conductors of the lead 110 and applied to tissue of a patient via stimulation electrodes 121a-d that are coupled to blocking capacitors. Any suitable known or later developed design may be employed for connector portion 171.

The stimulation electrodes 121a-d may be positioned along a horizontal axis 102 of the lead 110, and are angularly positioned about the horizontal axis 102 so the stimulation electrodes 121a-d do not overlap. The stimulation electrodes 121a-d may be in the shape of a ring such that each stimulation electrode 121a-d continuously covers the circumference of the exterior surface of the lead 110. Adjacent stimulation electrodes 121a-d are separated from one another by non-conducting rings 112, which electrically isolate each stimulation electrode 121a-d from an adjacent stimulation electrode 121a-d. The non-conducting rings 112 may include one or more insulative materials and/or biocompatible materials to allow the lead 110 to be implantable within the patient. Non-limiting examples of such materials include polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane. The stimulation electrodes 121a-d may be configured to emit the pulses in an outward radial direction proximate to or within a stimulation target. Additionally or alternatively, the stimulation electrodes 121a-d may be in the shape of a split or non-continuous ring such that the pulse may be directed in an outward radial direction adjacent to the stimulation electrodes 121a-d. The stimulation electrodes 121a-d deliver tonic, high frequency and/or burst nested stimulation waveforms as described herein. Optionally, the electrodes 121a-d may also sense neural oscillations and/or sensory action potential (neural oscillation signals) for a data collection window.

The lead 110 may comprise a lead body 172 of insulative material about a plurality of conductors within the material that extend from a proximal end of lead 110, proximate to the IMD 150, to its distal end. The conductors electrically couple a plurality of the stimulation electrodes 121 to a plurality of terminals (not shown) of the lead 110. The terminals are adapted to receive electrical pulses and the stimulation electrodes 121a-d are adapted to apply the pulses to the stimulation target of the patient. Also, sensing of physiological signals may occur through the stimulation electrodes 121a-d, the conductors, and the terminals. It should be noted that although the lead 110 is depicted with four stimulation electrodes 121a-d, the lead 110 may include any suitable number of stimulation electrodes 121a-d (e.g., less than four, more than four) as well as terminals, and internal conductors. Additionally or alternatively, various sensors (e.g., a position detector, a radiopaque fiducial) may be located near the distal end of the lead 110 and electrically coupled to terminals through conductors within the lead body 172.

Although not required for any embodiments, the lead body 172 of the lead 110 may be fabricated to flex and elongate upon implantation or advancing within the tissue (e.g., nervous tissue) of the patient towards the stimulation target and movements of the patient during or after implantation. By fabricating the lead body 172, according to some embodiments, the lead body 172 or a portion thereof is capable of elastic elongation under relatively low stretching forces. Also, after removal of the stretching force, the lead body 172 may be capable of resuming its original length and profile.

By way of example, the IMD 12, 150 may include a processor and associated charge control circuitry as described in U.S. Pat. No. 7,571,007, entitled "SYSTEMS AND METHODS FOR USE IN PULSE GENERATION," which is expressly incorporated herein by reference. Circuitry for recharging a rechargeable battery (e.g., battery charging circuitry 156) of an IMD using inductive coupling and external charging circuits are described in U.S. Pat. No. 7,212,110, entitled "IMPLANTABLE DEVICE AND SYSTEM FOR WIRELESS COMMUNICATION," which is expressly incorporated herein by reference. An example and discussion of "constant current" pulse generating circuitry (e.g., pulse generating circuitry 152) is provided in U.S. Patent Publication No. 20061/0170486 entitled "PULSE GENERATOR HAVING AN EFFICIENT FRACTIONAL VOLTAGE CONVERTER AND METHOD OF USE," which is expressly incorporated herein by reference. One or multiple sets of such circuitry may be provided within the IMD 12, 150. Different burst and/or high frequency pulses on different stimulation electrodes may be generated using a single set of the pulse generating circuitry using consecutively generated pulses according to a "multi-stimset program" as is known in the art. Complex pulse parameters may be employed such as those described in U.S. Pat. No. 7,228,179, entitled "Method and apparatus for providing complex tissue stimulation patterns," and International Patent Publication Number WO 2001/093953 A1, entitled "NEUROMODULATION THERAPY SYSTEM," which are expressly incorporated herein by reference. Alternatively, multiple sets of such circuitry may be employed to provide pulse patterns (e.g., tonic stimulation waveform, burst stimulation waveform) that include generated and delivered stimulation pulses through various stimulation electrodes of one or more leads as is also known in the art. Various sets of parameters may define the pulse characteristics and pulse timing for the pulses applied to the various stimulation electrodes. Although constant current pulse generating circuitry is contemplated for some embodiments, any other suitable type of pulse generating circuitry may be employed such as constant voltage pulse generating circuitry.

The controller 151 delivers a nested stimulation waveform to at least one electrode combination located proximate to nervous tissue of interest, the nested stimulation waveform including a series of pulses configured to excite the nested C-fibers of the nervous tissue of interest, the nested stimulation waveform defined by therapy parameters. The controller 151 may deliver the nested stimulation waveform based on preprogrammed therapy parameters. The preprogrammed therapy parameters may be set based on information collected from numerous past patients and/or test performed upon an individual patient during initial implant and/or during periodic checkups.

Optionally, the controller 151 senses intrinsic neural oscillations from at least one electrode on the lead. Optionally, the controller 151 analyzes the intrinsic neural oscillations signals to obtain brain activity data. The controller 151 determines whether the activity data satisfies a criteria of interest. The controller 151 adjusts at least one of the therapy parameters to change the nested stimulation waveform when the activity data does not satisfy the criteria of interest. The controller 151 iteratively repeats the delivering operations for a group of TPS. The IMD selects a candidate TPS from the group of TPS based on a criteria of interest. The therapy parameters define at least one of a burst stimulation waveform or a high frequency stimulation waveform. The controller 151 may repeat the delivering, sensing and adjusting operations to optimize the nested stimulation waveform. The analyzing operation may include analyzing a feature of interest from a morphology of the neural oscillation signal over time, counting a number of occurrences of the feature of interest that occur within the signal over a predetermined duration, and generating the activity data based on the number of occurrences of the feature of interest.

Memory 158 stores software to control operation of the controller 151 for nested stimulation therapy as explained herein. The memory 158 also stores neural oscillation signals, therapy parameters, neural oscillation activity level data, sensation scales and the like. For example, the memory 158 may save neural oscillation activity level data for various different therapies as applied over a short or extended period of time. A collection of neural oscillation activity level data is accumulated for different therapies and may be compared to identify high, low and acceptable amounts of sensory activity.

A controller device 160 may be implemented to charge/recharge the battery 154 of the IMD 150 (although a separate recharging device could alternatively be employed) and to program the IMD 150 on the pulse specifications while implanted within the patient. Although, in alternative embodiments separate programmer devices may be employed for charging and/or programming the NS system 100. The controller device 160 may be a processor-based system that possesses wireless communication capabilities. Software may be stored within a non-transitory memory of the controller device 160, which may be executed by the processor to control the various operations of the controller device 160. A "wand" 165 may be electrically connected to the controller device 160 through suitable electrical connectors (not shown). The electrical connectors may be electrically connected to a telemetry component 166 (e.g., inductor coil, RF transceiver) at the distal end of wand 165 through respective wires (not shown) allowing bi-directional communication with the IMD 150. Optionally, in some embodiments, the wand 165 may comprise one or more temperature sensors for use during charging operations.

The user may initiate communication with the IMD 150 by placing the wand 165 proximate to the NS system 100. Preferably, the placement of the wand 165 allows the telemetry system of the wand 165 to be aligned with the far-field and/or near field communication circuitry 155 of the IMD 150. The controller device 160 preferably provides one or more user interfaces 168 (e.g., touchscreen, keyboard, mouse, buttons, or the like) allowing the user to operate the IMD 150. The controller device 160 may be controlled by the user (e.g., doctor, clinician) through the user interface 168 allowing the user to interact with the IMD 150. The user interface 168 may permit the user to move electrical stimulation along and/or across one or more of the lead(s) 110 using different stimulation electrode 121 combinations, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME," which is expressly incorporated herein by reference.

Also, the controller device 160 may permit operation of the IMD 12, 150 according to one or more therapies to treat the patient. Each therapy may include one or more sets of stimulation parameters of the pulse including pulse amplitude, pulse width, pulse frequency or inter-pulse period, firing delay, pulse repetition parameter (e.g., number of times for a given pulse to be repeated for respective stimset during execution of program), biphasic pulses, monophasic pulses, etc. The IMD 150 modifies its internal parameters in response to the control signals from the controller device 160 to vary the stimulation characteristics of the stimulation pulses transmitted through the lead 110 to the tissue of the patient. NS systems, stimsets, and multi-stimset programs are discussed in PCT Publication No. WO 01/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are expressly incorporated herein by reference.

FIGS. 2A-2I illustrate example stimulation leads 14 that may be used for electrically stimulating the predetermined site to treat one or more neurological disorders or conditions.

As described above, each of the one or more stimulation leads 14 incorporated in stimulation systems 10, 100 includes one or more stimulation electrodes 18 adapted to be positioned in communication with the predetermined site and used to deliver the stimulation pulses received from IMD 12 (or pulse generating circuitry 157 in FIG. 1C). A percutaneous stimulation lead 14 (corresponding to the lead 110 in FIG. 1C), such as example stimulation leads 14a-d, includes one or more circumferential electrodes 18 spaced apart from one another along the length of stimulating portion 20 of stimulation lead 14. Circumferential electrodes 18 emit electrical stimulation energy generally radially (e.g., generally perpendicular to the axis of stimulation lead 14) in all directions. A laminotomy, paddle, or surgical stimulation lead 14, such as example stimulation leads 14e-i, includes one or more directional stimulation electrodes 18 spaced apart from one another along one surface of stimulation lead 14. Directional stimulation electrodes 18 emit electrical stimulation energy in a direction generally perpendicular to the surface of stimulation lead 14 on which they are located. Although various types of stimulation leads 14 are shown as examples, embodiments herein contemplate stimulation system 10 including any suitable type of stimulation lead 14 in any suitable number. In addition, stimulation leads 14 may be used alone or in combination. For example, medial or unilateral stimulation of the predetermined site may be accomplished using a single electrical stimulation lead 14 implanted in communication with the predetermined site in one side of the head, while bilateral electrical stimulation of the predetermined site may be accomplished using two stimulation leads 14 implanted in communication with the predetermined site in opposite sides of the head.

In one embodiment, the stimulation source is transcutaneously in communication with the electrical stimulation lead. In "transcutaneous" electrical nerve stimulation (TENS), the stimulation source is external to the patient's body, and may be worn in an appropriate fanny pack or belt, and the electrical stimulation lead is in communication with the stimulation source, either remotely or directly. In another embodiment, the stimulation is percutaneous. In "percutaneous" electrical nerve stimulation (PENS), needles are inserted to an appropriate depth around or immediately adjacent to a predetermined stimulation site, and then stimulated.

The IMD 12, 150 allow each electrode of each lead to be defined as a positive, a negative, or a neutral polarity. For each electrode combination (e.g., the defined polarity of at least two electrodes having at least one cathode and at least one anode), an electrical signal can have at least a definable amplitude (e.g., voltage), pulse width, and frequency, where these variables may be independently adjusted to finely select the sensory transmitting brain tissue required to inhibit transmission of neuronal signals. Generally, amplitudes, pulse widths, and frequencies are determinable by the capabilities of the neurostimulation systems, which are known by those of skill in the art. Voltages that may be used can include, for example about 0.5 to about 10 volts, more preferably about 1 to about 10 volts.

In embodiments herein, the therapy parameter of signal frequency is varied to achieve a burst type rhythm, or burst mode stimulation. Generally, the burst stimulus frequency may be in the range of about 1 Hz to about 100 Hz, more particular, in the range of about 1 Hz to about 12 Hz, and more particularly, in the range of about 1 Hz to about 4 Hz, 4 Hz to about 7 Hz or about 8 Hz to about 12 Hz for each burst. Each burst stimulus comprises at least two spikes, for example, each burst stimulus can comprise about 2 to about 100 spikes, more particularly, about 2 to about 10 spikes. Each spike can comprise a frequency in the range of about 50 Hz to about 1000 Hz, more particularly, in the range of about 200 Hz to about 500 Hz. The frequency for each spike within a burst can be variable, thus it is not necessary for each spike to contain similar frequencies, e.g., the frequencies can vary in each spike. The inter-spike interval can be also vary, for example, the inter-spike interval, can be about 0.5 milliseconds to about 100 milliseconds or any range therebetween.

The burst stimulus is followed by an inter-burst interval, during which substantially no stimulus is applied. The inter-burst interval has duration in the range of about 5 milliseconds to about 5 seconds, more preferably, 10 milliseconds to about 300 milliseconds. It is envisioned that the burst stimulus has a duration in the range of about 10 milliseconds to about 5 seconds, more particular, in the range of about 250 msec to 1000 msec (1-4 Hz burst firing), 145 msec to about 250 msec (4-7 Hz), 145 msec to about 80 msec (8-12 Hz) or 1 to 5 seconds in plateau potential firing. The burst stimulus and the inter-burst interval can have a regular pattern or an irregular pattern (e.g., random or irregular harmonics). More specifically, the burst stimulus can have a physiological pattern or a pathological pattern.

It is envisioned that the patient will require intermittent assessment with regard to patterns of stimulation. Different electrodes on the lead can be selected by suitable computer programming, such as that described in U.S. Pat. No. 5,938,690, which is incorporated by reference here in full. Utilizing such a program allows an optimal stimulation pattern to be obtained at minimal voltages. This ensures a longer battery life for the implanted systems.

FIGS. 2A-2I respectively depict stimulation portions for inclusion at the distal end of lead. Stimulation portion depicts a conventional stimulation portion of a "percutaneous" lead with multiple ring electrodes. Stimulation portion depicts a stimulation portion including several segmented electrodes. Example fabrication processes are disclosed in U.S. patent application Ser. No. 12/895,096, entitled, "METHOD OF FABRICATING STIMULATION LEAD FOR APPLYING ELECTRICAL STIMULATION TO TISSUE OF A PATIENT," which is incorporated herein by reference. Stimulation portion includes multiple planar electrodes on a paddle structure.

A. Deep Brain Stimulation

In certain embodiments, for example, patients may have an electrical stimulation lead or electrode implanted into the brain. The anatomical targets or predetermined site may be stimulated directly or affected through stimulation in another region of the brain.

In embodiments herein, the predetermined site or implant sites include, but are not limited to thalamus/sub-thalamus, basal ganglia, hippocampus, amygdala, hypothalamus, mammilary bodies, substantia nigra or cortex or white matter tracts afferent to or efferent from the abovementioned brain tissue, inclusive of the corpus callosum. Still further, the predetermined site may comprise the auditory cortex and/or somatosensory cortex in which the stimulation devices is implanted cortically.

Once electrical stimulation lead 14, 110 has been positioned in the brain, lead 14, 110 is uncoupled from any stereotactic equipment present, and the cannula and stereotactic equipment are removed. Where stereotactic equipment is used, the cannula may be removed before, during, or after removal of the stereotactic equipment. Connecting portion 16 of electrical stimulation lead 14, 110 is laid substantially flat along the skull. Where appropriate, any burr hole cover seated in the burr hole may be used to secure electrical stimulation lead 14, 110 in position and possibly to help prevent leakage from the burr hole and entry of contaminants into the burr hole.

Once electrical stimulation lead 14, 110 has been inserted and secured, connecting portion of lead 14, 110 extends from the lead insertion site to the implant site at which IMD 12, 150 is implanted. The implant site is typically a subcutaneous pocket formed to receive and house IMD 12, 150. The implant site is usually positioned a distance away from the insertion site, such as near the chest, below the clavicle or alternatively near the buttocks or another place in the torso area. Once all appropriate components of stimulation system 10, 100 are implanted, these components may be subject to mechanical forces and movement in response to movement of the person's body. A doctor, the patient, or another user of IMD 12, 150 may directly or indirectly input signal parameters for controlling the nature of the electrical stimulation provided.

Although example steps are illustrated and described, embodiments herein contemplate two or more steps taking place substantially simultaneously or in a different order. In addition, embodiments herein contemplate using methods with additional steps, fewer steps, or different steps, so long as the steps remain appropriate for implanting an example stimulation system 10, 100 into a person for electrical stimulation of the person's brain.

Brainstem Stimulation

The stimulation system 10, 100, described above, can be implanted into a person's body with stimulation lead 14 located in communication with a predetermined brainstem tissue and/or area. Such systems that can be used are described in WO2004062470, which is incorporated herein by reference in its entirety.

The predetermined brainstem tissue can be selected from medulla oblongata, pons or mesencephalon, more particular the posterior pons or posterior mesencephalon, Lushka's foramen, and ventrolateral part of the medulla oblongata.

Implantation of a stimulation lead 14 in communication with the predetermined brainstem area can be accomplished via a variety of surgical techniques that are well known to those of skill in the art. For example, an electrical stimulation lead can be implanted on, in, or near the brainstem by accessing the brain tissue through a percutaneous route, an open craniotomy, or a burr hole. Where a burr hole is the means of accessing the brainstem, for example, stereotactic equipment suitable to aid in placement of an electrical stimulation lead 14 on, in, or near the brainstem may be positioned around the head. Another alternative technique can include, a modified midline or retrosigmoid posterior fossa technique.

In certain embodiments, electrical stimulation lead 14 is located at least partially within or below the aura mater adjacent the brainstem. Alternatively, a stimulation lead 14 can be placed in communication with the predetermined brainstem area by threading the stimulation lead up the spinal cord column, as described above, which is incorporated herein.

As described above, each of the one or more leads 14 incorporated in stimulation system 10 includes one or more electrodes 18 adapted to be positioned near the target brain tissue and used to deliver electrical stimulation energy to the target brain tissue in response to electrical signals received from IMD 12. A percutaneous lead 14 may include one or more circumferential electrodes 18 spaced apart from one another along the length of lead 14. Circumferential electrodes 18 emit electrical stimulation energy generally radially in all directions and may be inserted percutaneously or through a needle. The electrodes 18 of a percutaneous lead 14 may be arranged in configurations other than circumferentially, for example as in a "coated" lead 14. A laminotomy or paddle style lead 14, such as example leads 14*e-i*, includes one or more directional electrodes 18 spaced apart from one another along one surface of lead 14. Directional electrodes 18 emit electrical stimulation energy in a direction generally perpendicular to the surface of lead 14 on which they are located. Although various types of leads 14 are shown as examples, embodiments herein contemplate stimulation system 10 including any suitable type of lead 14 in any suitable number, including three-dimensional leads and matrix leads as described below. In addition, the leads may be used alone or in combination.

Yet further, a stimulation lead 14 can be implanted in communication with the predetermined brainstem area by a using stereotactic procedures similar to those described above, which are incorporated herein, for implantation via the cerebrum.

Still further, a predetermined brainstem area can be in directly stimulated by implanting a stimulation lead 14 in communication with a cranial nerve (e.g., olfactory nerve, optic, nerve, oculomoter nerve, trochlear nerve, trigeminal nerve, abducent nerve, facial nerve, vestibulocochlear nerve, glossopharyngeal nerve, vagal nerve, accessory nerve, and the hypoglossal nerve) as well as high cervical nerves (cervical nerves have anastomoses with lower cranial nerves) such that stimulation of a cranial nerve in directly stimulates the predetermined brainstem tissue. Such techniques are further described in U.S. Pat. Nos. 6,721,603; 6,622,047; and 5,335,657, and U.S. Provisional Application 60/591,195 entitled "Stimulation System and Method for Treating a Neurological Disorder" each of which are incorporated herein by reference.

Although example steps are illustrated and described, embodiments herein contemplate two or more steps taking place substantially simultaneously or in a different order. In addition, embodiments herein contemplate using methods with additional steps, fewer steps, or different steps, so long as the steps remain appropriate for implanting stimulation system 10 into a person for electrical stimulation of the predetermined site.

In accordance with embodiments herein, methods and devices afford activation of the anti-nociceptive system of the human body. For example, the methods and systems may utilize nested stimulation therapies to treat chronic neuropathic pain, various syndromes, fibromyalgia, and in general nociceptive pain. By activating pleasure responses of the human body, methods and devices are provided to treat depression, social isolation or deprivation, distress, anxiety, autism and the like. Further, by activating pleasure responses of the human body, methods and devices are provided to treat homeostatic imbalances, such as irritable bowel syndrome (IBS), urinary urgency, pain, tinnitus, addiction, obesity and the like.

A. Sensory Disorders 1. Tinnitus

In the auditory system, tonic firing transmits the contents of auditory information, while burst firing transmit the valence or importance attached to that sound (Lisman 1997; Sherman 2001; Swadlow and Gusev 2001). Repetitive stimulus presentation results in decreased neuronal response to that stimulus, known as auditory habituation at the single cell level (Ulanovsky et al., 2003), auditory mismatch negativity at multiple cell level (Naatanen et al., 1993; Ulanovsky et al., 2003).

Tinnitus is a noise in the ears, often described as ringing, buzzing, roaring, or clicking Subjective and objective forms of tinnitus exist, with objective tinnitus often caused by muscle contractions or other internal noise sources in the area proximal to auditory structures. In certain cases, external observers can hear the sound generated by the internal source of objective tinnitus. In subjective forms, tinnitus is audible only to the subject. Tinnitus varies in perceived amplitude, with some subjects reporting barely audible forms and others essentially deaf to external sounds and/or incapacitated by the intensity of the perceived noise.

Tinnitus is usually constantly present, e.g., a non-rational valence is attached to the internally generated sound, and there is no auditory habituation to this specific sound, at this specific frequency. Thus, tinnitus is the result of hyperactivity of lesion-edge frequencies, and auditory mismatch negativity in tinnitus patients is specific for frequencies located at the audiometrically normal lesion edge (Weisz 2004).

As pathological valence of the tinnitus sound is mediated by burst firing, burst firing is increased in tinnitus in the extralemniscal system (Chen and Jastreboff 1995; Eggermont and Kenmochi 1998; Eggermont 2003), in the inner hair cells (Puel 1995; Puel et al., 2002), the auditory nerve (Moller 1984), the dorsal and external inferior colliculus (Chen and Jastreboff 1995), the thalamus (Jeanmonod, Magnin et al., 1996) and the secondary auditory cortex (Eggermont and Kenmochi 1998; Eggermont 2003). Furthermore, quinine, known to generate tinnitus, induces an increased regularity in burst firing, at the level of the auditory cortex, inferior colliculus and frontal cortex (Gopal and Gross 2004). It is contemplated that tinnitus can only become conscious if an increased tonic firing rate is present in the lemniscal system, generating the sound. This increased firing activity has been demonstrated in the lemniscal dorsal cochlear nucleus (Kaltenbach, Godfrey et al., 1998; Zhang and Kaltenbach 1998; Kaltenbach and Afman 2000; Brozoski, Bauer et al., 2002; Zacharek et al., 2002; Kaltenbach et al., 2004), inferior colliculus (Jastreboff and Sasaki 1986; Jastreboff, Brennan et al., 1988; Jastreboff 1990) (Gerken 1996) and primary auditory cortex (Komiya, 2000). Interestingly, not only tonic firing is increased generating the tinnitus sound, but also the burst firing (Ochi and Eggermont 1997) (keeping it conscious) at a regular basis. Repetitive burst firing is known to generate tonic gamma band activity (Gray and Singer 1989; Brumberg, 2000). Thus, it is envisioned that embodiments herein can be used to modify burst firing, thus modifying tonic gamma activity.

Burst mode firing boosts the gain of neural signaling of important or novel events by enhancing transmitter release and enhancing dendritic depolarization, thereby increasing synaptic potentiation. Conversely, single spiking mode may be used to dampen neuronal signaling and may be associated with habituation to unimportant events (Cooper 2002). It is believed that the main problem in tinnitus is that the internally generated stimulus does not decay due to the presence of regular bursting activity telling the cortex this signal is important and has to remain conscious.

Thus, in embodiments herein, it is envisioned that the neuromodulation system can attack either of these two pathways: slowing down tonic firing in the lemniscal system (below 40 Hz) or removing the valence attached to it by the extralemniscal system by suppressing the regular bursting rhythm, thereby treating tinnitus. Yet further, the neuromodulation system of embodiments herein can also make the tinnitus disappear via auditory habituation. Suppressing the rhythmic burst firing in the frontal cortex may after the emotional affect given to the tinnitus, with the tinnitus persisting, a situation known by many people perceiving tinnitus, but without much influence on their daily life. Such methods of treating tinnitus are further described in U.S. Provisional Applications entitled "Deep Brain Stimulation to Treat Tinnitus" filed Oct. 21, 2004; "Peripheral Nerve Stimulation to Treat Tinnitus" filed Oct. 21, 2004; and "Dorsal Column Stimulation to Treat Tinnitus" filed Oct. 21, 2004, each of which is incorporated by reference in its entirety. 2. Phantom Pain In phantom pain the same is noted as in Parkinson's Disease (PD) and tinnitus. In humans, the tonic firing rate increases (Yamashiro et al., 2003), as well as the amount of burst firing in the deafferented receptive fields (Rinaldi et al., 1991; Jeanmonod et al., 1996; Radhakrishnan et al., 1999) in the somatosensory thalamic nuclei (Rinaldi et al., 1991; Lenz et al., 1998), as well as activity in the in the intralaminar nuclei (Weigel and Krauss 2004). Synchrony in firing is also increased. This is similar to what is seen in animal neuropathic pain models (Lombard and Besson 1989; Nakamura and Atsuta 2004) (Yamashiro et al., 1991). These results suggest that in pain decreased spike frequency adaptation and increased excitability develops after injury to sensory neurons. Through decreased $Ca^{2+}$ influx, the cell becomes less stable and more likely to initiate or transmit bursts of action potentials (McCallum et al., 2003).

Thus, it is envisioned that that the neuromodulation system or method of embodiments herein will alter or disrupt the regular bursting rhythm associated with the phantom pain.
3. Motor Disorders In Parkinson's disease (PD), the striatum is viewed as the principal input structure of the basal ganglia, while the internal pallidal segment (GPi) and the substantia nigra pars reticulata (SNr) are output structures. Input and output structures are linked via a monosynaptic "direct" pathway and a polysynaptic "indirect" pathway involving the external pallidal segment (GPe) and the subthalamic nucleus (STN). According to current schemes, striatal dopamine (DA) enhances transmission along the direct pathway (via D1 receptors), and reduces transmission over the indirect pathway (via D2 receptors) (Wichmann and DeLong 2003).

Increased firing rates are noted in PD, both in the globus pallidus (Magnin et al., 2000) and the subthalamic nucleus (Levy et al., 2002) and is reversed in successful STN stimulation in PD (Welter et al., 2004; Boraud et al., 1996). Synchronization between firing rates is important: lower frequency oscillations facilitate slow idling rhythms in the motor areas of the cortex, whereas synchronization at high frequency restores dynamic task-related cortical ensemble activity in the gamma band (Brown 2003). In PD, a (hyper) synchronization is related to tremor (Levy et al., 2002), similarly to what is seen in the animal Parkinson model (Raz et al., 2000; Nini et al., 1995).

Two or more firing modes exist in the subthalamic nucleus: tonic firing (68%), phasic or burst firing (25%) and phasic-tonic (7%) (Magarinos-Ascone et al., 2002).

In the monkey MPTP Parkinson model, burst firing, which occurs at 4 to 8 Hz, increases in the STN and Gpi in comparison to normal firing (from 69% and 78% in STN and GPi to 79% and 89%, respectively) (Bergman et al., 1994), as well as burst duration, without increase in the amount of spikes per burst (Bergman et al., 1994). Abnormally increased tonic and phasic activity in STN leads to abnormal GPi activity and is a major factor in the development of parkinsonian motor signs (Wichmann et al., 1994). The percentage of cells with 4- to 8-Hz periodic activity correlates with tremor and is significantly increased from 2% to 16% in STN and from 0.6% to 25% in GPi with the MPTP treatment (Bergman et al., 1994). These cells are also recorded in humans with PD (Hutchison et al., 1997). Furthermore, synchronization increases, e.g., a decrease in independent activity (Raz et al., 2000; Nini et al., 1995), both in tonically firing cells (Raz et al., 2001) and burst firing cells. Thus, it is envisioned that that the neuromodulation or stimulation system or method of embodiments herein will alter or disrupt or override the regular bursting rhythm associated with PD.

Other movement disorders, for example, chorea, Huntington's chorea, hemiballism and parkinsonian tremor all differ in the amount of regularity in their muscle contractions. (Hashimoto and Yanagisawa 1994). The regularities of interval, amplitude, rise time, and EMG activity differs within order of regularity, such PD, vascular chorea, Huntington chorea and hemiballism being least regular (Hashimoto and Yanagisawa 1994). However, in chorea (Hashimoto et al., 2001), hemiballism (Postuma and Lang 2003) and Huntington's disease (Cubo et al., 2000), the firing rate might be decreased in contrast to PD. Burst discharges are, however, correlated to the choreatic movements (Kanazawa et al., 1990), similarly to what is noted in PD (Bergman, Wichmann et al., 1994). Thus, the neuromodulation system and/or method of embodiments herein is used to alter or disrupt the dysfunctional firing rate of the disease or condition.

B. Autonomic Disorders

The autonomic nervous system (ANS) is predominantly an efferent system transmitting impulses from the central nervous system (CNS) to peripheral organ systems. Its effects include control of heart rate and force of contraction, constriction and dilatation of blood vessels, contraction and relaxation of smooth muscle in various organs, visual accommodation, pupillary size and secretions from exocrine and endocrine glands. In addition to it being predominantly an efferent system, there are some afferent autonomic fibers (e.g., transmit information from the periphery to the CNS), which are concerned with the mediation of visceral sensation and the regulation of vasomotor and respiratory reflexes, for example the baroreceptors and chemoreceptors in the carotid sinus and aortic arch which are important in the control of heart rate, blood pressure and respiratory activity. These afferent fibers are usually carried to the CNS by major autonomic nerves such as the vagus, splanchnic or pelvic nerves, although afferent pain fibers from blood vessels may be carried by somatic nerves.

The ANS is divided into two separate divisions, the parasympathetic and sympathetic systems. This division is based on anatomical and functional differences. Both of these systems consist of myelinated preganglionic fibres that make synaptic connections with unmyelinated postganglionic fibres, and it is these which then innervate the effector organ. These synapses usually occur in dusters called ganglia. Most organs are innervated by fibers from both divisions of the ANS, and the influence is usually opposing (e.g., the vagus slows the heart, whilst the sympathetic nerves increase its rate and contractility), although it may be parallel (e.g., the salivary glands).

The activity recorded from mammalian sympathetic nerves comes in bursts, which result from large numbers of fibers firing synchronously. Human sympathetic nerve activity behaves similarly. Vasomotor, cardiac and sudomotor nerve fibers all fire in bursts. Bursts in post-ganglionic nerves are driven by synchronously firing preganglionic neurons. Burst amplitude, which reflects the number of fibers firing together, and burst probability are controlled independently (McAllen and Malpas 1997). The sympathetic nerve also fires in a 10 Hz tonic mode (Barman, Kitchens et al., 1997). This 10-Hz rhythm is also involved in cardiovascular regulation, as blood pressure falls significantly when the 10-Hz rhythm is eliminated. Cardiac-related burst activity and 10-Hz rhythms are generated by different pools of brainstem neurons (Barman, Kitchens et al., 1997).

When electrical stimulation is applied to the sympathetic nerve, burst stimulation is more powerful (vasoconstrictor) than tonic mode. The amount of spikes per burst also determines the efficacy of stimulation (Ando, Imaizumi et al., 1993). The same is seen with electrical stimulation of the cervical sympathetic nerve trunk delivered at 50 Hz in bursts of 1 s every 10 s. Burst stimulation evoked a more copious, uniform and reproducible flow of saliva than when delivered at 10 Hz continuously (Anderson, Garrett et al., 1988). Similar superior results with burst stimulation have been obtained studying nasal mucosa reactivity: both types of stimulation reduced nasal blood flow and volume, but the responses were significantly larger with burst stimulation at 0.59 Hz compared to tonic 0.59 Hz stimulation (Lacroix, Stjame et al., 1988).

In the parasympathetic system, burst firing and tonic firing co-exist. For example, one population of neurons responds with a brief burst of action potentials at the onset of the depolarization, accommodating to the stimulus, and the other population responds with repetitive action potentials persisting throughout the duration of the stimulus, not accommodating to the stimulus (Myers 1998; Bertrand 2004).

Burst stimulation at 0.1 Hz with 20 Hz spiking of the parasympathetic nerve results in a 200-fold more powerful enzyme induction than 2 Hz tonic stimulation, when delivering the same amount of pulses (in the sublingual gland) (Nilsson, Rosengren et al., 1991). 1. Hypertension and Heart Rhythm Disorders The nucleus of the solitary tract (NTS), a termination site for primary afferent fibers from baroreceptors and other peripheral cardiovascular receptors, and the paratrigeminal nucleus (Pa5) contain blood pressure-sensitive neurons, some of which have rhythmic activity locked to the cardiac cycle, making them key components of the central pathway for cardiovascular regulation. NTS and Pa5 baroreceptor-activated neurons possess phasic discharge patterns locked to the cardiac cycle (Junior, Caous et al., 2004). The human insular cortex is involved in cardiac regulation. The left insula is predominantly responsible for parasympathetic cardiovascular effects. On stimulation of the left insular cortex, parasympathetic tone increases resulting in bradycardia and depressor responses more frequently than tachycardia and pressor effects ($p<0.005$) (Oppenheimer, Gelb et al., 1992). The converse applies for the right insular cortex: stimulation of the human right insula increases sympathetic cardiovascular tone (Oppenheimer 1993). Acute left insular stroke increases basal cardiac sympathetic tone and is associated with a decrease in randomness of heart rate variability (Oppenheimer, Kedem et al., 1996). Increased sympathoadrenal tone, resulting from damage to cortical areas involved in cardiac and autonomic control can induce cardiac damage by nonischemic mechanisms (Oppenheimer and Hachinski 1992).

Brain noradrenaline (NA) neurons in the locus coeruleus (LC) and major parts of the SNS respond by burst activation in concert to stressful stimuli implying novelty or fear. (Svensson 1987). In hypertension, burst firing is increased (Schlaich, Lambert et al., 2004) (Esler, Rumantir et al., 2001).

The autonomic nervous system plays an important role in the genesis of various cardiac rhythm disorders. In patients with paroxysmal atrial fibrillation, it is important to distinguish vagally mediated from adrenergically mediated atrial fibrillation. The former is considered to represent a form of lone atrial fibrillation affecting particularly males aged 40 to 50 years. The arrhythmic episodes manifest themselves most often during the night lasting from minutes to hours, whereas in adrenergic mediated atrial fibrillation, atrial fibrillation is often provoked by emotional or physical stress. (Hohnloser, van de Loo et al., 1994)

Thus, hypertension (e.g., neurogenic hypertension) can be treated with burst stimulation of the left insula using the stimulation system of embodiments herein. In a similar fashion, bradycardia can be treated by burst stimulation of the right insula as subjects with bradycardia have significantly higher metabolic activity in the right (p<0.0001) and in the left temporal insula (p<0.015) than those with normal heart rates (Volkow, Wang et al., 2000). Lone atrial fibrillation can be treated by either by left or rightsided burst stimulation depending on whether it is vagally or adrenergicly induced. 2. Sleep Apnea Activity in the sympathetic nervous system is enhanced not only in obstructive apnea, but also in central and mixed apnea (Shimizu, Takahashi et al., 1997). Burst rate during apnea is higher in central apneas than in obstructive apneas. Burst rate is the central component of mixed apnea and the obstructive component of mixed apneas (Shimizu, Takahashi et al., 1997).

This intense sympathoexcitation is due to chronic or intermittent hypoxia (Cutler, Swift et al., 2004; Cutler, Swift et al., 2004). Pathological sympathoexcitation appears to depend on both recruitment and increased burst firing frequency. In OSAS, also the amount of spikes per burst is increased, (Elam, McKenzie et al., 2002) and at night, arousal-induced reduction in sympathetic burst latency is noted (Xie, Skatrud et al., 1999).

Functional MRI or FMRI studies demonstrate reduced neural signals within the frontal cortex, anterior cingulate, cerebellar dentate nucleus, dorsal pons, anterior insula and lentiform nuclei. Signal increases in OSA over control subjects are seen in the dorsal midbrain, hippocampus, quadrangular cerebellar lobule, ventral midbrain and ventral pons (Macey, Macey et al., 2003). In the rat, the respiratory area in the anterior insular cortex consists of two distinct zones which overlap a region modulating the gastrointestinal activity (Aleksandrov, Aleksandrova et al., 2000). In the more rostral area, there is a decrease in respiratory airflow and tidal volume with no alteration of the respiratory rate (the inhibition response), and in the other there is an increase in respiratory rate and inspiratory airflow (the excitation response).

Thus, embodiments herein can be used to activate respiration during apneas by burst stimulation of the anterior insula.

C. Obesity

Food presentation in normal healthy, non-obese individuals significantly increases metabolism in the whole brain (24%, P<0.01), and these changes are largest in superior temporal, anterior insula, and orbitofrontal cortices (Wang, Volkow et al., 2004). Food-related visual stimuli elicit greater responses in the amygdala, parahippocampal gyms and anterior fusiform gyms when participants are in a hungry state relative to a satiated state (LaBar, Gitelman et al., 2001). Hunger is associated with significantly increased rCBF in the vicinity of the hypothalamus and insular cortex and in additional paralimbic and limbic areas (orbitofrontal cortex, anterior cingulate cortex, and parahippocampal and hippocampal formation), thalamus, caudate, precuneus, putamen, and cerebellum (Tataranni, Gautier et al., 1999). Satiation is associated with increased rCBF in the vicinity of the ventromedial prefrontal cortex, dorsolateral prefrontal cortex, and inferior parietal lobule (Tataranni, Gautier et al., 1999). High-calorie foods yield significant activation within the medial and dorsolateral prefrontal cortex, thalamus, hypothalamus, corpus callosum, and cerebellum. Low-calorie foods yield smaller regions of focal activation within medial orbitofrontal cortex, primary gustatory/somatosensory cortex, and superior, middle, and medial temporal regions (Killgore, Young et al., 2003). Activity within the temporo-insular cortex in normal appetitive function is associated with the desirability or valence of food stimuli, prior to ingestion (Gordon, Dougherty et al., 2000). When a food is eaten to satiety, its reward value decreases. Responses of gustatory neurons in the secondary taste area within the orbitofrontal cortex are modulated by hunger and satiety, in that they stop responding to the taste of a food on which an animal has been fed to behavioral satiation, yet may continue to respond to the taste of other foods (Critchley and Rolls 1996; O'Doherty, Rolls et al., 2000). In the OFC, the rCBF decreases in the medial OFC and increases in the lateral OFC as the reward value of food changes from pleasant to aversive for non-liquid (Small, Zatorre et al., 2001) and liquid foods (Kringelbach, O'Doherty et al., 2003). In the insular gustatory cortex, neuronal responses to gustatory stimuli are not influenced by the normal transition from hunger to satiety. This is in contrast to the responses of a population of neurons recorded in the hypothalamus, which only respond to the taste of food when the monkey is hungry (Yaxley, Rolls et al., 1988). Brain responses to hunger/satiation in the hypothalamus, limbic/paralimbic areas (commonly associated with the regulation of emotion), and prefrontal cortex (thought to be involved in the inhibition of inappropriate response tendencies) might be different in obese and lean individuals (Del Parigi, Gautier et al., 2002). Compared with lean women, obese women have significantly greater increases in rCBF in the ventral prefrontal cortex and have significantly greater decreases in the paralimbic areas and in areas of the frontal and temporal cortex (Gautier, Del Parigi et al., 2001). In obese women, the rCBF is higher in the right parietal and temporal cortices during the food exposure than in the control condition. In addition, in obese women the activation of the right parietal cortex is associated with an enhanced feeling of hunger when looking at food (Karhunen, Lappalainen et al., 1997). This significantly higher metabolic activity in the bilateral parietal somatosensory cortex is noted in the regions where sensation to the mouth, lips and tongue are located. The enhanced activity in somatosensory regions involved with sensory processing of food in the obese subjects can make them more sensitive to the rewarding properties of food related to palatability and can be one of the variables contributing to their excess food consumption (Wang, Volkow et al., 2002).

Based on the abovementioned model, the stimulation system and/or method of embodiments herein can be used to produce burst stimulation of the—orbitofrontal cortex or—insula to treat obesity especially in those people who are constant eaters rather than binge or high volume eaters. Other targets that can be stimulated are the dorsolateral prefrontal cortex, thalamus, hypothalamus, corpus callosum, and cerebellum, as well as the medial orbitofrontal cortex, primary gustatory/somatosensory cortex, and superior, middle, and medial temporal regions and the amygdalohippocampal area and anterior cingulated area.

D. Cognitive and Psychological Disorders 1. Depression

In patients suffering from a depression, a hypometabolism and hypoperfusion localized to the left middorsolateral frontal cortex (MDLFC) is noted (Baxter, Schwartz et al., 1989; Brody, Saxena et al., 2001). Furthermore decreased neural activity in the MDLFC, aka the dorsolateral prefrontal cortex, is correlated with severity of depression (Bench, Friston et al., 1992; Bench, Friston et al., 1993; Dolan, Bench et al., 1994) and is reversed upon recovery from depression (Bench, Frackowiak et al., 1995). Electroencephalography demonstrates increased alpha power. Alpha power is thought to be inversely related to neural activity in left frontal regions of the brains of depressed patients (Bruder, Fong et al., 1997).

Metabolic activity in the ventral perigenual ACC is increased in depressed patients relative to control subjects (Videbech, Ravnkilde et al., 2001) and is positively correlated with severity of depression (Drevets 1999). Furthermore, neural activity in this region decreases in response to antidepressant treatment (Brody, Saxena et al., 2001).

The MDLFC occupies the middle frontal and superior frontal gyri and comprises cytoarchitectonic areas 46 and 9/46 (middle frontal gyms) and area 9 (superior frontal gyms) (Paus and Barrett 2004). The MDLFC has connections with sensory areas processing visual (prestriate and inferior temporal cortices), auditory (superior temporal cortex) and somatosensory (parietal cortex) information (Petrides and Pandya 1999). The MDLFC also reciprocally connects with the anterior and, to a lesser extent, posterior cingulate cortices (Bates and Goldman-Rakic 1993).

Transcranial magnetic stimulation has been performed in the treatment of depression. The left MDLFC is the most common target for rTMS treatment of depression (Paus and Barrett 2004), and rTMS of the left MDLFC modulates the blood-flow response in the ACC (Barrett, Della-Maggiore et al., 2004; Paus and Barrett 2004). High-frequency (20 Hz) and low-frequency (1 Hz) stimulation seem to have an opposite effect. High-frequency stimulation (HFS) increases and low-frequency stimulation (LFS) decreases cerebral blood flow (CBF) and/or glucose metabolism in the frontal cortex and other linked brain regions (Speer, Kimbrell et al., 2000; Kimbrell, Little et al., 1999; and Post, Kimbrell et al., 1999).

Successful treatment of depression with TMS results in normalization of hypoperfusion (with HFS) and normalization hyperperfusion (with LFS) (Kimbrell, Little et al., 1999). Thus, TMS treatment for depression can be proposed using 20 Hz left frontal cortex (Kimbrell, Little et al., 1999; Paus and Barrett 2004) or 1 Hz right frontal cortex (Klein, Kreinin et al., 1999).

In the ACC of the rat, three kinds of burst firing is recorded. Rhythmic burst firing with inter-burst intervals of 80 and 200 ms and non-rhythmic burst firing (Gemmell, Anderson et al., 2002). ACC stimulations evoke both tonic and burst reactions in the dorsolateral prefrontal cortex (Desiraju 1976). Similarly to other cortical areas, the dorsolateral prefrontal cortex has burst firing cells, tonic firing cells and mixed firing cells. Similarly to other areas, the burst firing notices new incoming sensory (auditory, visual) information, and tonic firing continues as long as the stimulus lasts (Ito 1982). TMS in burst mode is more powerful than TMS in tonic mode. For example, 20 seconds of 5 Hz burst firing with 3 pulses at 50 Hz per burst have the same effect as 10 minutes 1 Hz tonic TMS.

Thus, the present stimulation system and/or method can be used to treat depression. For example, a cortical electrode is implanted on the right MDLFC and a 5 Hz burst mode is used to treat recurring depressions that react to a test stimulation with TMS. 2. Obsessive Convulsive Disorder Obsessive-compulsive disorder is a worldwide psychiatric disorder with a lifetime prevalence of 2% and mainly characterized by obsessional ideas and compulsive behaviors and rituals. Bilateral stimulation in the anterior limbs of the internal capsules (Nuttin, Cosyns et al., 1999; Nuttin, Gabriels et al., 2003) or nucleus accumbens stimulation (Sturm, Lenartz et al., 2003) can improve symptoms but at high frequency and high intensity stimulation. Thus, embodiments herein can be used to produce burst mode stimulation to treat an obsessive-compulsive disorder. 3. Tourette's Syndrome Tourette syndrome (TS) is a neuropsychiatric disorder with onset in early childhood. It is characterized by tics and often accompanied by disturbances in behavior, such as obsessive-compulsive disorder (OCD). Bilateral thalamic stimulation, with promising results on tics and obsessive-compulsive symptoms has been performed as a treatment. (Visser-Vandewalle, Temel et al., 2003; Temel and Visser-Vandewalle 2004). Thus, it is envisioned that the stimulation system and/or method of embodiments herein can be used to treat TS.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) execute program instructions stored in memory (for example, software stored on a tangible and non-transitory computer readable storage medium, such as a computer hard drive, ROM, RAM, or the like).

The processor(s) may execute a set of instructions that are stored in one or more storage elements, in order to process data. The storage elements may also store data or other information as desired or needed. The storage element may be in the form of an information source or a physical memory element within the controllers and the controller device. The set of instructions may include various commands that instruct the controllers and the controller device to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

The controller may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. When processor-based, the controller executes program instructions stored in memory to perform the corresponding operations. Additionally or alternatively, the controllers and the controller device may represent circuits that may be implemented as hardware. The above examples are exemplary only, and are thus not intended to limit in any way the definition and/or meaning of the term "controller."

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 45 U.S.C. § 112(f), unless and until such claim limitations expressly use the phrase "means for" followed by a statement of function void of further structure.

What is claimed is:

1. A method to deliver nested stimulation to nerve tissue of interest, the method comprising:
    setting one or more first parameters that define a carrier waveform;
    setting one or more second parameters that define a high frequency waveform, wherein at least one of the carrier waveform and high frequency waveform are defined to correspond to physiologic neural oscillations associated with the nerve tissue of interest;
    operating a pulse generator to generate a nested stimulation waveform that combines the carrier waveform and high frequency waveform, the nested stimulation waveform having a plurality of pulse bursts, wherein (1) each of the pulse bursts comprise a plurality of discrete pulses, (2) pulses within each pulse burst are repeated according to a frequency parameter of the high frequency waveform, and (3) an amplitude of each discrete pulse within respective pulse bursts is controlled according to nesting of the high frequency waveform with the carrier waveform such that amplitude peaks of the corresponding plurality of discrete pulses vary within each respective pulse burst; and
    delivering the nested stimulation waveform through one or more electrodes to the nerve tissue of interest of a patient.

2. The method of claim 1, wherein the nerve tissue of interest includes brain tissue of interest, and wherein the high frequency waveform corresponds to high-frequency physiologic neural oscillations associated with brain tissue of interest, and wherein the pulse bursts including pulses have a frequency corresponding to the high frequency neural oscillations.

3. The method of claim 1, wherein the carrier waveform corresponds to low-frequency physiologic neural oscillations associated with the nerve tissue of interest.

4. The method of claim 3, wherein the pulse bursts are separated from one another with a burst to burst period that corresponds to a frequency of the low-frequency neural oscillations.

5. The method of claim 1, wherein the first one or more parameters and the second one or more parameters define at least one of an amplitude, burst to burst frequency, pulse frequency, pulse width, burst length and burst period for the plurality of pulse bursts.

6. The method of claim 1, wherein the first one or more parameters are set to define the carrier waveform to correspond to a theta wave frequency band, while the second one or more parameters are set to define the high-frequency waveform to correspond to a gamma wave frequency band.

7. The method of claim 1, wherein the nerve tissue of interest includes brain tissue of interest, and further comprising:
    detecting an event of interest through cross frequency coupling between theta and gamma waves associated with brain tissue of interest and
    managing the nested stimulation waveform in connection with detection of the event of interest through cross frequency coupling between theta and gamma waves associated with brain tissue of interest.

8. The method of claim 1, wherein the nerve tissue of interest includes brain tissue of interest, and wherein the brain tissue of interest comprises distributed neural modifies located in separate regions of the brain, the method further comprising:
    detecting cross frequency coupling between neural oscillations associated with the distributed neural modifies that exhibit long-distance communication over neural oscillations within at least one of delta, theta and alpha wave frequency bands; and
    managing the nested stimulation waveform in connection with detection of the cross frequency coupling between neural oscillations associated with the distributed neural modules.

9. The method of claim 1, wherein the carrier waveform is formed with a first waveform and a second waveform with the first waveform having a frequency of less than 1 Hz and the second waveform has a frequency of 12 Hz or less, and wherein the high frequency waveform has a frequency of 12 Hz or higher.

* * * * *